US011466248B2

(12) United States Patent
Lee et al.

(10) Patent No.: US 11,466,248 B2
(45) Date of Patent: Oct. 11, 2022

(54) STREPTOMYCES COELICOLOR MUTANT STRAIN, METHOD OF PRODUCING β-AGARASE BY USING SAME, AND METHOD OF PRODUCING NEOAGARO-OLIGOSACCHARIDES BY USING SAME

(71) Applicant: DYNEBIO INC., Seongnam-si (KR)

(72) Inventors: Je Hyeon Lee, Seongnam-si (KR); Eun Joo Kim, Seongnam-si (KR); Yeon Hee Lee, Seongnam-Si (KR)

(73) Assignee: DYNEBIO INC., Seongnam-si (KR)

( * ) Notice: Subject to any disclaimer, the term of this patent is extended or adjusted under 35 U.S.C. 154(b) by 69 days.

(21) Appl. No.: 16/980,042

(22) PCT Filed: Sep. 10, 2019

(86) PCT No.: PCT/KR2019/011722
§ 371 (c)(1),
(2) Date: Sep. 11, 2020

(87) PCT Pub. No.: WO2020/060098
PCT Pub. Date: Mar. 26, 2020

(65) Prior Publication Data
US 2021/0009940 A1 Jan. 14, 2021

(30) Foreign Application Priority Data
Sep. 19, 2018 (KR) .................. 10-2018-0112517

(51) Int. Cl.
*C12N 1/20* (2006.01)
*C12P 19/04* (2006.01)
*C12P 19/14* (2006.01)

(52) U.S. Cl.
CPC .............. *C12N 1/20* (2013.01); *C12P 19/04* (2013.01); *C12P 19/14* (2013.01); *C12Y 302/01081* (2013.01)

(58) Field of Classification Search
CPC . C12N 1/20; C12P 19/04; C12P 19/14; C12Y 302/01081
See application file for complete search history.

(56) References Cited

U.S. PATENT DOCUMENTS 4,532,208 A * 7/1985 Hafner ............... C12N 9/92
435/234
9,617,592 B2 * 4/2017 Van Wezel ............ C12Q 1/02

FOREIGN PATENT DOCUMENTS

| KR | 10-1233766 B1 | 2/2013 |
| KR | 10-1261852 B1 | 5/2013 |
| KR | 10-2018-0019881 A | 2/2018 |
| KR | 10-1919962 B1 | 2/2019 |
| WO | 2015/041498 A1 | 3/2015 |

OTHER PUBLICATIONS

Hong, SJ et al. "Safety evaluation of beta-agarase preparations from *Streptomyces coelicolor* A3(2)", Regulatory Toxicology and Pharmacology, 2019, vol. 101, pp. 142-155. (Year: 2019).*
Hong et al. "Toxicological evaluation of neoagarooligosaccharides prepared by enzymatic hydrolysis of agar", Regulatory Toxicology and Pharmacology, 2017, vol. 90, pp. 9-21 (Year: 2017).*
Gascon et al. "Purification of the internal invertase of yeast", Journal of biological chemistry, 1968, vol. 243, issue 7, pp. 1567-1572 (Year: 1968).*
Azin, M., Noroozi, E. "Random mutagenesis and use of 2-deoxy-D-glucose as an antimetabolite for selection of α-amylase-overproducing mutants of Aspergillus oryzae." World Journal of Microbiology and Biotechnology, 2001, 17, 747-750. https://doi.org/10.1023/A:1012928707998 (Year: 2001).*
International Search Report for PCT/KR2019/011722 dated Dec. 24, 2019 (PCT/ISA/210).

* cited by examiner

*Primary Examiner* — Neil P Hammell
*Assistant Examiner* — Deepa Mishra
(74) *Attorney, Agent, or Firm* — Sughrue Mion, PLLC

(57) ABSTRACT

The present invention provides *Streptomyces coelicolor* strain A3(2)_M22-2C43 obtained by inducing a point mutation in the base sequence of the DagB gene in a wild-type *Streptomyces coelicolor* strain A3(2) by UV radiation. Since the *Streptomyces coelicolor* strain A3(2)_M22-2C43 according to the present invention expresses a DagB mutant enzyme expressing little or no DagB beta-agarase or exhibiting little or no beta-agarase activity, there is no need for separate isolation and purification of DagA enzymes from culture fluid, and the culture fluid of the *Streptomyces coelicolor* strain A3(2)_M22-2C43 or supernatant thereof may be used to produce, from agar or agarose, neoagarose oligosaccharides with a higher content of neoagarotetraose or neoagarohexaose than that of neoagarobiose.

8 Claims, 9 Drawing Sheets
Specification includes a Sequence Listing.

[FIG. 1]
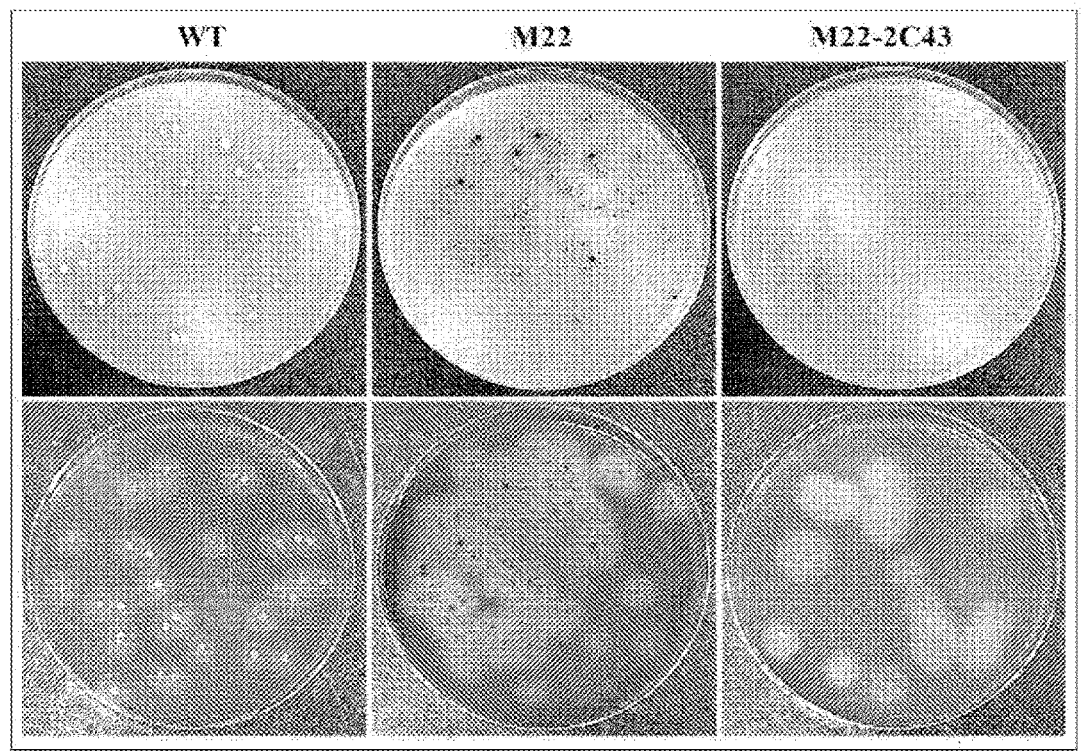
[FIG. 2]
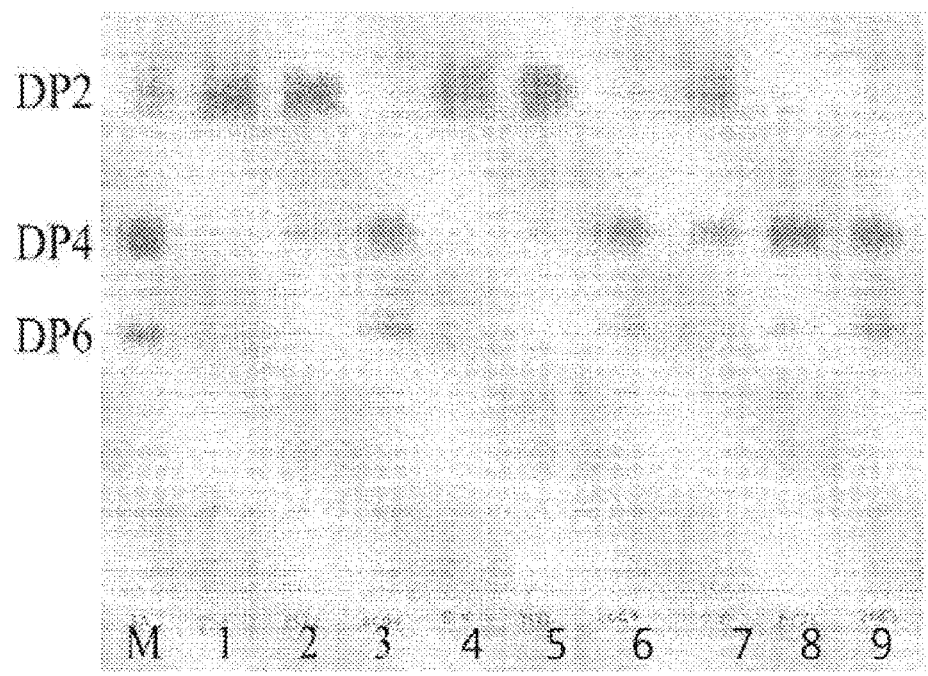

[FIG. 4]

```
1201 CCCGACACCCTGGCCGGTCCCGTCGCGCAGGGCGAGACCTACAGCTTCTACAAGGCGAAC
     ************************************************************
1201 CCCGACACCCTGGCCGGTCCCGTCCCGTCGCGAGGGCGAGACCTACAGCTTCTACAAGGCGAAC

1261 GTCGCCCGGAAGTACCCCGGCAGCAACTACATGAGCGGTGGCGGGACAACACGGTCGAC
     ************************************************************
1261 GTCGCCCGGAAGTACCCCGGCAGCAACTACATGAGCGGTGGCGGGACAACACGGTCGAC

1321 CGGATGCTCAGCTGGGGGCTTCACCTCCTTCGGCAACTGGACCGACCCGGAGATGTACGAC
     ************************************************************
1321 CGGATGCTCAGCTGGGGGCTTCACCTCCTTCGGCAACTGGACCGACCCGGAGATGTACGAC

1381 AACGACCGTATCCCGTACTTCGCCCACGGCTGGATCAAGGGCGACTTCAAGACGGTGAGC
     ************************************************************
1381 AACGACCGTATCCCGTACTTCGCCCACGGCTGGATCAAGGGCGACTTCAAGACGGTGAGC

1441 ACCGGCCAGGACTACTGGGGCCCGATGCCGGACCCCGTTCGACCCCGCGTTCTCCGACGCC
     ************************************************************
1441 ACCGGCCAGGACTACTGGGGCCCGATGCCGGACCCCGTTCGACCCCGCGTTCTCCGACGCC

1501 GCAGCCAGAACCGGCGAGCAGTCGCCGACGAGGTCGCCGACAGCCCGGTTGGCGATCGGC
     ************************************************************
1501 GCAGCCAGAACCGGCGAGCAGTCGCCGACGAGGTCGCCGACAGCCCGGTTGGCGATCGGC
```

[FIG. 5]
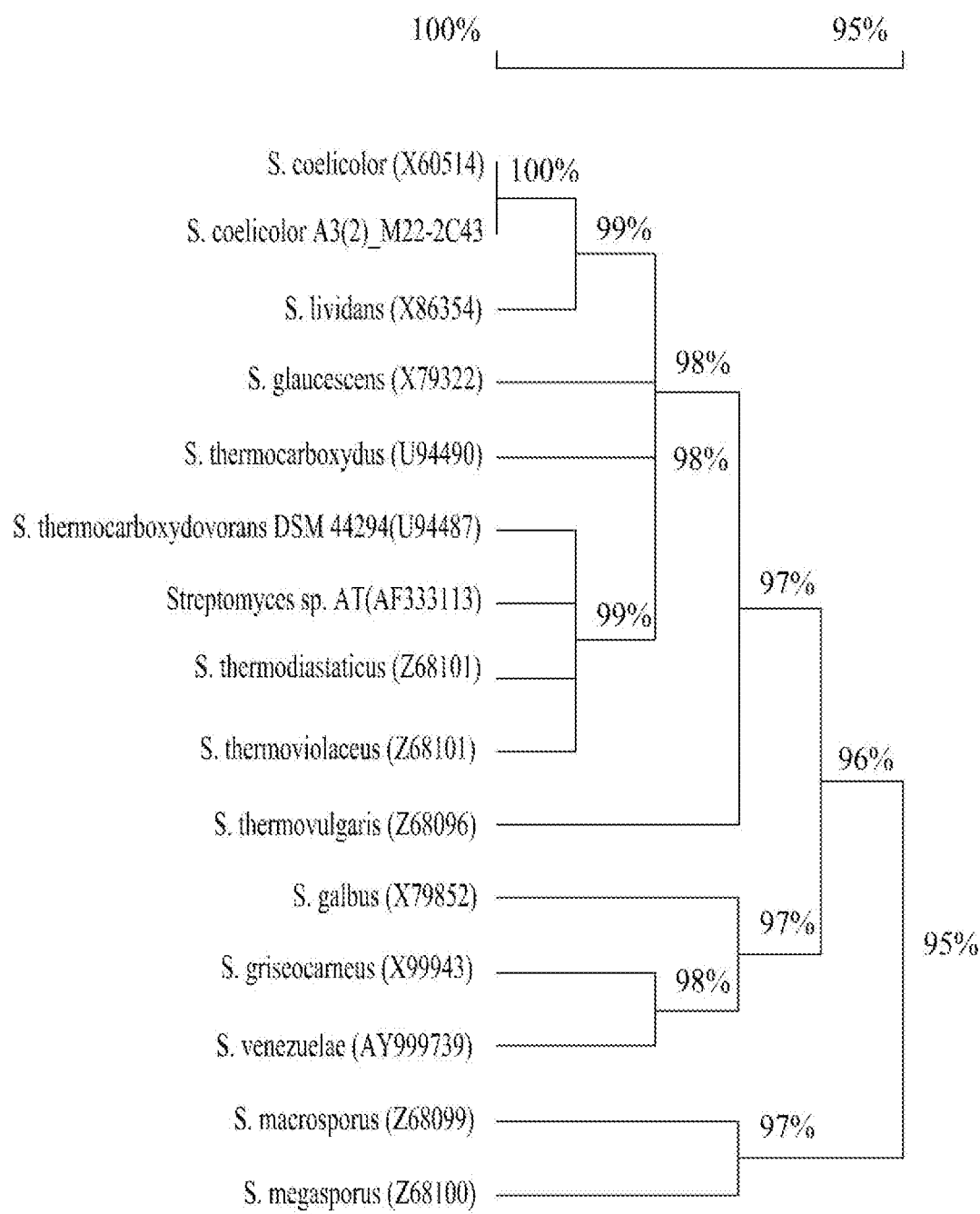

[FIG. 6]
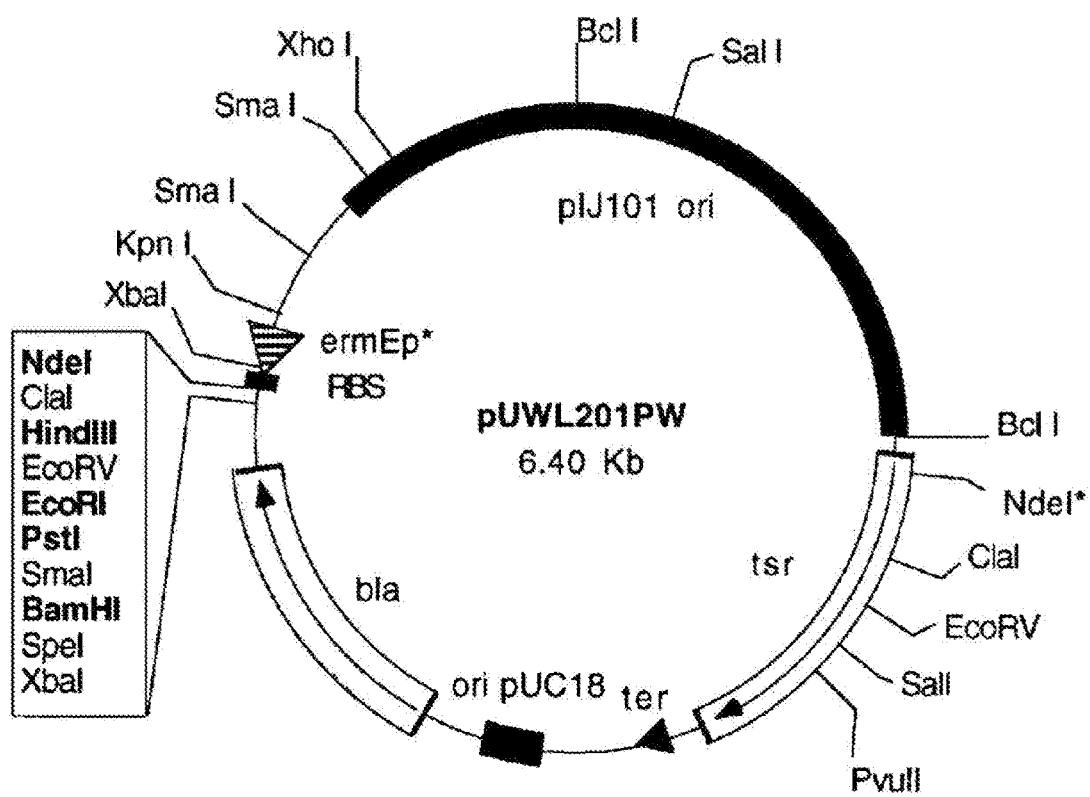

[FIG. 7]
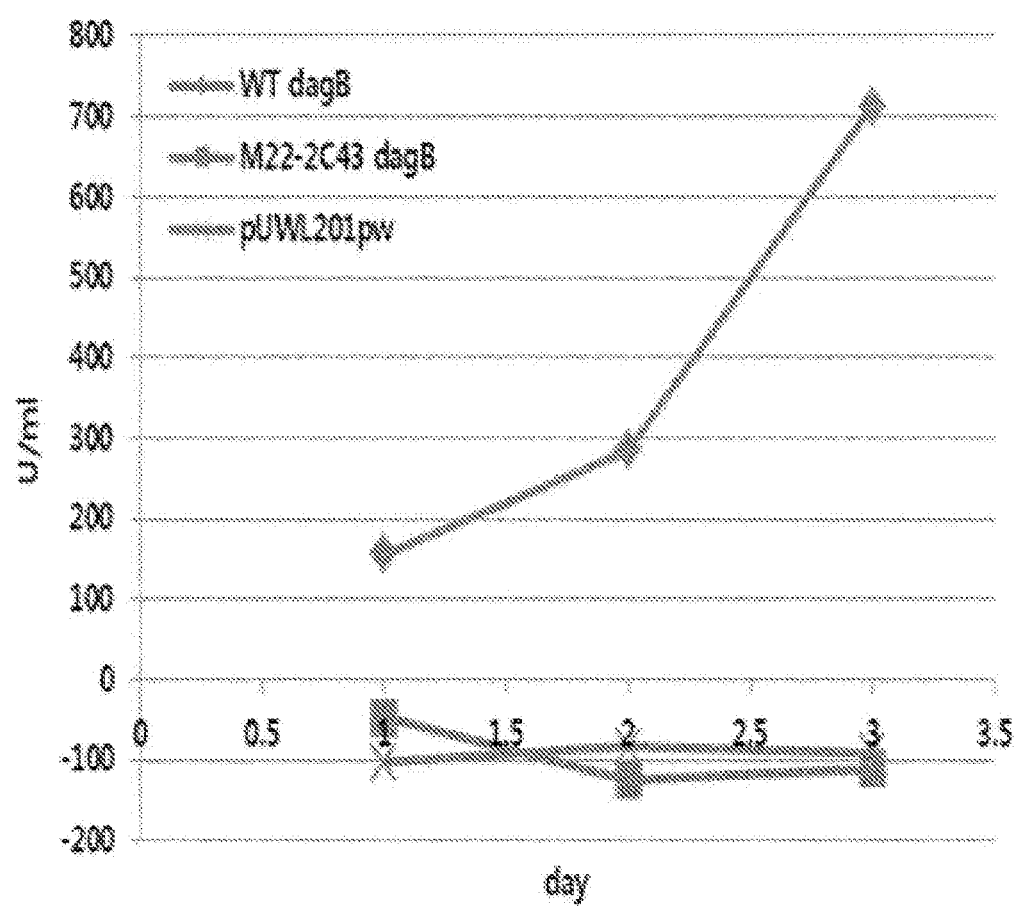

STREPTOMYCES COELICOLOR MUTANT STRAIN, METHOD OF PRODUCING β-AGARASE BY USING SAME, AND METHOD OF PRODUCING NEOAGARO-OLIGOSACCHARIDES BY USING SAME

CROSS REFERENCE TO RELATED APPLICATIONS

This application is a National Stage of International Application No. PCT/KR2019/011722 filed Sep. 10, 2019, claiming priority based on Korean Patent Application No. 10-2018-0112517 filed Sep. 19, 2018, the entire disclosures of which are incorporated herein by reference.

TECHNICAL FIELD

The present disclosure relates to a *Streptomyces coelicolor* mutant strain, a method for producing β-agarase using the same, and a neoagarooligosaccharide preparation method using the same. More specifically, the present disclosure relates to the *Streptomyces coelicolor* mutant strain which mainly expresses DagA enzyme compared to a parent strain, a method of producing a large amount of DagA enzyme in β-agarase using the same, and a method of preparing neoagarooligosaccharide with a higher content of neoagarotetraose or neoagarohexaose than that of neoagarobiose from agar or agarose using the same.

BACKGROUND ART

Agar is a representative seaweed-derived polysaccharide that has been widely used as food additives, pharmaceuticals, cosmetics, livestock feed and industrial raw materials since long ago. In Korea, the agar is one of the relatively abundant fishery resources with the annual production amount of about 2,000 to 5,000 tons. However, in terms of actual use thereof, only a portion of the total production volume is simply processed and used as cheap raw materials. Most of the rest thereof is wasted, and thus an added value thereof is very low compared to the amount of endowed resources thereof. Therefore, research on the development of new uses of abundant domestic agar and improvement of the added value thereof is in great demand.

Agar is composed mostly of polysaccharides except for a small amount of protein, ash and fat. Polysaccharides constituting the agar include agarose as a neutral polysaccharide, and agaropectin as an acidic polysaccharide. The agarose has a unit of agarobiose in which D-galactose and 3,6-anhydro-L-galactose are bound to each other in a β-1,4 form. In the agarose, the agarobioses as the units are repeatedly connected to each other using α-1,3 bond to form a linear structure. Thus, the agarose has higher gelation ability. To the contrary, the agaropectin has agarobiose as a unit as in the agarose, but contains acidic groups such as sulfuric acid groups. Thus, the gelation ability thereof is weak. The agarose is decomposed to neoagarotetraose and then to neoagarobiose using β-agarase that acts on the β-1,4 bond, and then is finally decomposed into D-galactose and 3,6-anhydro-L-galactose using alpha-agarase acting on the α-1,3 bond. Further, agarose is decomposed into agarobiose using dilute acid or alpha-agarase. In general, neoagarooligosaccharide refers to oligosaccharides containing 2 to 10 monosaccharides coupled to each other such as neoagarobiose, neoagarotetraose, neoagarohexaose, neoagarooctaose, etc., as obtained by hydrolyzing the agar or agarose with the β-agarase. Further, agarooligosaccharide refers to an oligosaccharide in which 2 to 10 monosaccharides are bound to each other, such as agarobiose, agarotetraose, agarohexaose, agarooctaose, etc. as obtained by hydrolyzing the agar or agarose with dilute acid or alpha-agarase. The neoagarooligosaccharide has 3,6-anhydro-L-galactose as a non-reducing terminal, while agarooligosaccharide has D-galactose as a non-reducing terminal. Because of this structural difference, they may show different properties in terms of physiological activity.

Further, the actinomyces *Streptomyces coelicolor* A3(2) is known to produce β-agarase that degrades agar or agarose in the form of extracellular (secreted out of cells) protein (Stanier et al., 1942, J. Bacteriol.; Hodgson and Chater, 1981, J. Gen. Microbiol.). The agarase is encoded using a DagA gene or DagB gene. DagA enzyme in the β-agarase as produced by the *Streptomyces coelicolor* A3(2) decomposes the agar or agarose to produce mainly DP4 (neoagarotetraose) and DP6 (neoagarohexaose), while DagB enzyme in the β-agarase decomposes agar or agarose to mainly produce DP2 (neoagarobiose). Among the β-agarase based reaction products of agar or agarose, DP4 (neoagarotetraose) and DP6 (neoagarohexaose) have higher improving effect of metabolic diseases such as anti-obesity, anti-diabetes, and hyperlipidemia, and higher anti-cancer, and higher immunity enhancing effect than DP2 (neoagarobiose) has. Thus, the DagA gene has an important role in the study of producing agarase using actinomyces. In particular, *Streptomyces coelicolor* is the most widely used strain in molecular biology studies of actinomyces. The sequence of chromosomal DNA thereof was analyzed by the British Sanger Center in 2002 and is now published (Bantley et al., 2002, Nature).

Regarding the preparation or use of neoagarooligosaccharide, Korean Patent No. 10-0794593 discloses a method of preparing at least one type of neoagarooligosaccharide selected from the group consisting of neoagarobiose, neoagarotetraose and neoagarohexaose using *Thalassomonas* sp. SL-5 KCCM 10790P having agar decomposition ability and β-agarase produced by the strain. Further, Korean patent No. 10-1072503 discloses a method for preparing one or more neoagarooligosaccharides using the strain *Glaciecola* sp. SL-12 KCCM 10945P having agar decomposition ability and β-agarase produced by the strain, wherein one or more neoagarooligosaccharides are selected from the group consisting of neoagarobiose, neoagarotetraose and neoagarohexaose. Further, Korean patent No. 10-1303839 discloses a method of producing at least one neoagarooligosaccharide selected from the group consisting of neoagarotetraose and neoagarohexaose using *Pseudoalteromonas* sp strain and the β-agarase isolated from the *Pseudoalteromonas* sp strain. Further, Korean patent No. 10-1295659 discloses a method for producing neoagarooligosaccharide using *Saccharophagus* sp. strain and β-agarase isolated from *Saccharophagus* sp. strain, wherein the neoagarooligosaccharide includes at least one selected from the group consisting of neoagarotetraose and neoagarohexaose. Further, Korean patent No. 10-1212106 discloses a method of producing neoagarobiose by reacting β-agarase isolated from *Saccharophagus* sp. strain with at least one substrate selected from the group consisting of agar, neoagarotetraose, and neoagarohexaose. Further, Korean patent No. 10-1206006 discloses a method for preparing one or more neoagarooligosaccharides by reacting *Flammeovirga* sp. mbrc-1 KCCM 11151P having agar degrading activity and β-agarase produced by the strain with agar, wherein one or more neoagarooligosaccharides are selected from the group consisting of neoagarobiose, neoagarotetraose, and neoagarohexaose. Further, Korean patent No. 10-1302655 discloses a method for producing neoagarotetraose and neoagarohexaose by reacting *Streptomyces coelicolor*-derived agarase and agarose or agar with each other. Further, Korean patent No. 10-1190078 discloses a β-agarase recombinant expression vector capable of transforming prokaryotes, wherein the vector contains a DNA fragment represented by the base sequence represented by SEQ ID NO:7 comprising the promoter and signal peptide coding region of *Streptomyces griseus*-derived trypsin gene (sprT); and a DNA fragment represented by the base sequence represented by SEQ ID NO:2 from which the signal peptide coding region has been removed from the *Streptomyces coelicolor*-derived β-agarase gene (dagA), and discloses a method for producing β-agarase using the vector. Further, Korean Laid-Open Patent Publication No. 10-2014-0060045 discloses a method for enzymatically producing neoagarobiose or neoagarotetraose using a novel β-agarase producing gene. Further, Korean Patent Application Publication No. 10-2009-0044987 discloses a skin whitening composition containing neoagarotetraose as an active ingredient. Further, Korean Patent Application Publication No. 10-2013-0085017 discloses a pharmaceutical composition for the prevention or treatment of skin pigmentation disorders containing 3,6-anhydro-L-galactose, a skin whitening or moisturizing cosmetic composition containing 3,6-anhydro-L-galactose, and a pharmaceutical composition for preventing or treating inflammatory diseases containing 3,6-anhydro-L-galactose. As described above, in the prior art, in order to prepare the neoagarooligosaccharide having a relatively higher content of neoagarotetraose and neoagarohexaose than that of neoagarobiose from agar or agarose, a transformed strain was prepared using gene recombination or a method of separating and purifying only DagA in the β-agarase expressed via new or recombinant strain has been used. To date, no strains capable of producing DagA β-agarase at a commercially applicable level have been reported.

DISCLOSURE

Technical Problem

The present disclosure is derived from the above technical background. Thus, one purpose of the present disclosure is to provide a *Streptomyces coelicolor* mutant strain that mainly expresses DagA β-agarase which is relatively highly active, compared to the parent strain, and which rarely expresses DagB β-agarase.

Further, one purpose of the present disclosure is to provide a method for producing DagA β-agarase efficiently and in large quantities using the *Streptomyces coelicolor* mutant strain.

Further, one purpose of the present disclosure is to provide a method of preparing a neoagarooligosaccharide with a relatively higher content of neoagarotetraose or neoagarohexaose than that of neoagarobiose from agar or agarose using the *Streptomyces coelicolor* mutant strain.

Technical Solution

The present inventors irradiated the wild-type *Streptomyces coelicolor* A3(2) strain with ultraviolet rays to induce mutations thereof and first selected *Streptomyces coelicolor* A3(2)_M22 strain overexpressing the β-agarase among the mutations and filed a patent application thereof (Korean Laid-Open Patent Publication No. 10-2018-0019881, 2018 Feb. 27). The present disclosure refers to all the contents disclosed in Korean Laid-Open Patent Publication No. 10-2018-0019881 with respect to the selection and technical characteristics of the *Streptomyces coelicolor* A3(2)_M22 strain. The first selected *Streptomyces coelicolor* A3(2)_M22 strain was identified as expressing both DagA β-agarase and DagB β-agarase. Thereafter, the first selected *Streptomyces coelicolor* A3(2)_M22 strain was again irradiated with ultraviolet rays to induce mutations thereof. Among the mutations, *Streptomyces coelicolor* A3(2)_M22-2C43 strain which mainly expresses highly active DagA β-agarase and rarely expresses DagB β-agarase or expresses DagB mutant enzyme with little β-agarase activity was finally selected. In this way, the present disclosure has been completed.

In order to achieve the above purpose, one example of the present disclosure provides *Streptomyces coelicolor* A3(2) M22-2C43 strain (accession number: KCCM 12577P) in which the β-agarase activity of the culture fluid obtained by culturing the strain under the same conditions or the β-agarase activity of the supernatant collected from the culture fluid is at least 1.2 times, preferably 1.4 times or greater than that of the wild-type *Streptomyces coelicolor* strain, wherein the *Streptomyces coelicolor* A3(2)_M22-2C43 strain mainly expresses DagA β-agarase and rarely expresses DagB β-agarase or expresses DagB mutant enzyme that does not have β-agarase activity, compared to wild-type *Streptomyces coelicolor* strain or *Streptomyces coelicolor* A3(2)_M22 strain (accession number: KFCC 11668P). The *Streptomyces coelicolor* A3(2)_M22-2C43 strain according to one example of the present disclosure may be obtained through various known mutation methods. Preferably, the wild-type *Streptomyces coelicolor* A3(2) parent strain was mutated by irradiation ultraviolet rays thereto. Specifically, the *Streptomyces coelicolor* A3(2)_M22-2C43 strain according to one example of the present disclosure may be obtained by a method in which the wild-type *Streptomyces coelicolor* A3(2) parent strain is irradiated with ultraviolet rays to obtain a mutated *Streptomyces coelicolor* A3(2)_M22 strain and then the *Streptomyces coelicolor* A3(2)_M22 strain is subjected to irradiation with ultraviolet rays and thus is mutated. The *Streptomyces coelicolor* A3(2)_M22-2C43 strain according to one example of the present disclosure may produce β-agarase with significantly improved activity compared to the wild-type *Streptomyces coelicolor* A3(2) parent strain, or may express β-agarase in a remarkably higher level compared to the parent strain. Further, the *Streptomyces coelicolor* A3(2)_M22-2C43 strain according to one example of the present disclosure has a DagB gene (see SEQ ID NO:2) modified by a point mutation in which guanine (G) as a 1420-th DNA base sequence of a normal DagB gene (see SEQ ID NO: 1) is substituted with cytosine (C), compared with wild-type *Streptomyces coelicolor* strain or *Streptomyces coelicolor* A3(2)_M22 strain (accession number: KFCC 11668P). Further, the DagB gene modified by the gene mutation and contained in the *Streptomyces coelicolor* A3(2)_M22-2C43 strain (refer to SEQ ID NO:2) is expressed as a DagB mutant enzyme that is rarely expressed during strain culture or has no β-agarase activity. Specifically, wild-type *Streptomyces coelicolor* strain or *Streptomyces coelicolor* A3(2)_M22 strain (accession number: KFCC 11668P) expresses DagB β-agarase composed of the amino acid sequence represented by SEQ ID NO:5. To the contrary, *Streptomyces coelicolor* A3(2)_M22-2C43 strain expresses a DagB mutant enzyme composed of the amino acid sequence represented by SEQ ID NO:6 corresponding to the modified DagB gene (see SEQ ID NO:2). In the DagB mutant enzyme composed of the amino acid sequence represented by SEQ ID NO:6, glycine (G) as the 474-th amino acid is substituted with arginine (R) when compared to the normal DagB β-agarase composed of the amino acid sequence represented by SEQ ID NO:5. It was identified that the DagB mutant enzyme had no β-agarase activity, and especially no activity to decompose agar or agarose to convert to DP2 (neoagarobiose).

Because the *Streptomyces coelicolor* A3(2)_M22-2C43 strain according to one example of the present disclosure has the DagB gene modified by gene mutation, it mainly expresses DagA β-agarase and rarely expresses DagB β-agarase or expresses DagB mutant enzyme with little β-agarase activity. Therefore, using the culture fluid of *Streptomyces coelicolor* A3(2)_M22-2C43 strain according to one example of the present disclosure or the supernatant of the culture fluid, neoagarooligosaccharide with a relatively higher content of neoagarotetraose or neoagarohexaose than that of neoagarobiose may be prepared from agar or agarose.

In order to achieve the above purpose, one example of the present disclosure provides a method for producing β-agarase, the method including (a) inoculating and culturing the aforementioned *Streptomyces coelicolor* A3(2)_M22-2C43 strain into a liquid culture medium containing galactose as a carbon source to obtain a culture fluid, and (b) centrifuging the culture fluid to obtain a supernatant. In the method for producing β-agarase according to one example of the present disclosure, a concentration of galactose in the liquid culture medium is preferably 0.5% (w/v) to 4% (w/v) in consideration of the β-agarase activity of the culture fluid or supernatant collected from the culture fluid. In consideration of the DagA enzymic activity of the culture fluid or the supernatant collected from the culture fluid, the concentration is more preferably 1.0% (w/v) to 2.5% (w/v). Further, in the method for producing β-agarase according to one example of the present disclosure, a culture temperature of the *Streptomyces coelicolor* A3(2)_M22-2C43 strain is preferably 25 to 35° C., and more preferably 28 to 32° C. in consideration of the β-agarase activity of the culture fluid or supernatant collected from the culture fluid. Further, in the method for producing β-agarase according to one example of the present disclosure, a culturing agitation speed of the *Streptomyces coelicolor* A3(2)_M22-2C43 strain is preferably 200 to 300 rpm, and more preferably 210 to 270 rpm in consideration of the β-agarase activity of the culture fluid or supernatant collected from the culture fluid. Further, in the method for producing β-agarase according to one example of the present disclosure, a culturing duration of the *Streptomyces coelicolor* A3(2)_M22-2C43 strain is preferably 40 to 150 hr, and more preferably 48 to 120 hr, in consideration of the β-agarase activity of the collected supernatant.

Further, another example of the present disclosure provides a method for producing β-agarase, the method including (a) inoculating and culturing the aforementioned *Streptomyces coelicolor* A3(2)_M22-2C43 strain into a liquid culture medium containing galactose as a carbon source to obtain a culture fluid; (b) centrifuging the culture fluid to obtain a supernatant; and (c) adding ammonium sulfate to the supernatant to precipitate the β-agarase contained in the supernatant. In the method for producing β-agarase according to another example of the present disclosure, a concentration of galactose in the liquid culture medium is preferably 0.5% (w/v) to 4% (w/v) in consideration of the β-agarase activity of the culture fluid or supernatant collected from the culture fluid. In consideration of the DagA enzymic activity of the culture fluid or the supernatant collected from the culture fluid, the concentration is more preferably 1.0% (w/v) to 2.5% (w/v). Further, in the method for producing β-agarase according to another example of the present disclosure, the culture temperature of the *Streptomyces coelicolor* A3(2)_M22-2C43 strain is preferably 25 to 35° C. in consideration of the β-agarase activity of the culture fluid or supernatant collected from the culture fluid. It is more preferable that it is 28 to 32° C. Further, in the method for producing β-agarase according to another example of the present disclosure, a culturing agitation speed of the *Streptomyces coelicolor* A3(2)_M22-2C43 strain is preferably 200 to 300 rpm, and more preferably, 210 to 270 rpm in consideration of the β-agarase activity of the culture fluid or supernatant collected from the culture fluid. Further, in the method for producing β-agarase according to another example of the present disclosure, the culturing duration of the *Streptomyces coelicolor* A3(2)_M22-2C43 strain is preferably 40 to 150 hr, and more preferably 48 to 120 hr in consideration of the β-agarase activity of the collected supernatant. Further, in the method for producing β-agarase according to another example of the present disclosure, the ammonium sulfate is added so that the protein saturation concentration of the supernatant is preferably 45% to 70% in consideration of the β-agarase activity of the product purified from the supernatant of the culture fluid. When considering the DagA enzymic activity of the product purified from the supernatant of the culture fluid, it is more preferable to add the supernatant so that the protein saturation concentration is 45% to 55%.

To achieve the above purpose, one example of the present disclosure provides a neoagarooligosaccharide preparation method including (a') preparing a culture fluid of *Streptomyces coelicolor* A3(2)_M22-2C43 strain or a supernatant of the culture fluid; and (b') performing enzymatic reaction of agar or agarose with the β-agarase present in the culture fluid of the *Streptomyces coelicolor* A3(2)_M22-2C43 strain or the supernatant of the culture fluid. In the neoagarooligosaccharide preparation method according to one example of the present disclosure, the culture fluid may be obtained by inoculating and culturing the above-described *Streptomyces coelicolor* A3(2)_M22-2C43 strain into a liquid culture medium containing galactose as a carbon source. Further, in the neoagarooligosaccharide preparation method according to one example of the present disclosure, the enzyme reaction temperature is preferably 30 to 45° C., and more preferably 35 to 42° C.

Advantageous Effects

When using the *Streptomyces coelicolor* A3(2)_M22-2C43 strain according to the present disclosure, it is possible to produce a large amount of β-agarase which has very high activity. Further, the *Streptomyces coelicolor* A3(2)_M22-2C43 strain according to the present disclosure rarely expresses DagB β-agarase or expresses the DagB mutant enzyme having no β-agarase activity (especially, no activity to decompose agar or agarose to convert to DP2 (neoagarobiose). Thus, there is no need to separate and purify DagA enzyme from the culture fluid. The *Streptomyces coelicolor* A3(2)_M22-2C43 strain culture fluid or the supernatant thereof may be used to prepare the neoagarooligosaccharide with a relatively higher content of neoagarotetraose or neoagarohexaose than that of neoagarobiose from agar or agarose.

DESCRIPTION OF DRAWINGS

FIG. 1 is a photograph showing the colony morphology of each of *Streptomyces coelicolor* A3(2) wild-type (WT)

strain, *Streptomyces coelicolor* A3(2)_M22 strain, and *Streptomyces coelicolor* A3(2) M22-2C43 strain. A picture in a lower row in FIG. 1 shows the result of staining colonies with a dyeing reagent.

FIG. 2 shows analysis results of the DagA enzymic activity of each of supernatant samples obtained through culture of *Streptomyces coelicolor* A3(2) wild-type (WT) strain, *Streptomyces coelicolor* A3(2)_M22 strain and *Streptomyces coelicolor* A3(2)_M22-2C43 strain, a 50% ASP sample (an enzyme sample obtained by adding ammonium sulfate so that the saturation concentration of the protein contained in the supernatant becomes 50%), and a 70% ASP sample (an enzyme sample obtained by adding ammonium sulfate so that the saturation concentration of the protein contained in the supernatant is 70%) using a thin layer chromatography (TLC) method.

Figure 3:
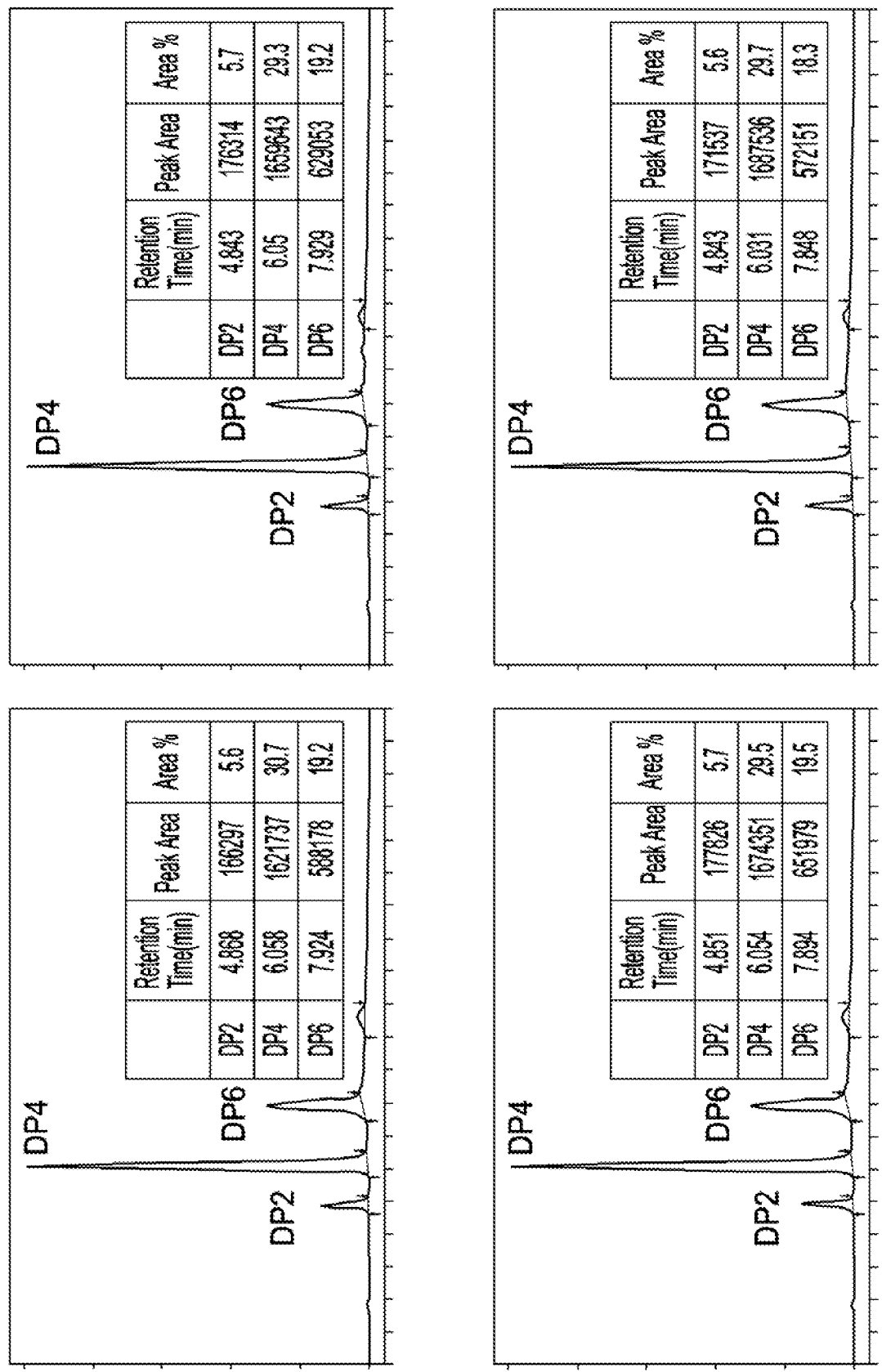

FIG. 3 shows an analyzing result of a composition of neo-agarosaccharide in a degradation product using HPLC-ELSD, wherein the degradation product is obtained by reacting agarose with a 70% ASP sample obtained through culture of *Streptomyces coelicolor* A3(2)_M22-2C43 strain.

FIG. 4 shows some of comparison results of the DagB gene base sequence (upper line; positions 1201-1560 of SEQ ID NO: 1) of the *Streptomyces coelicolor* A3(2) wild-type (WT) strain and the DagB gene base sequence (lower line; positions 1201-1560 of SEQ ID NO: 2) of the *Streptomyces coelicolor* A3(2)_M22-2C43 strain as aligned with each other.

FIG. 5 shows the biological lineage and relationship of the *Streptomyces coelicolor* A3(2)_M22-2C43 strain prepared based on the 16S rRNA base sequence.

FIG. 6 is a cleavage map of the pUWL201pw vector used to clone the DagB gene according to the present disclosure.

FIG. 7 shows the β-agarase activity of each of supernatants obtained from culture of recombinant strain WT dagB, recombinant strain M22-2C43 dagB and recombinant strain pUWL201pw prepared in the examples of the present disclosure based on the culture date.

Figure 8:
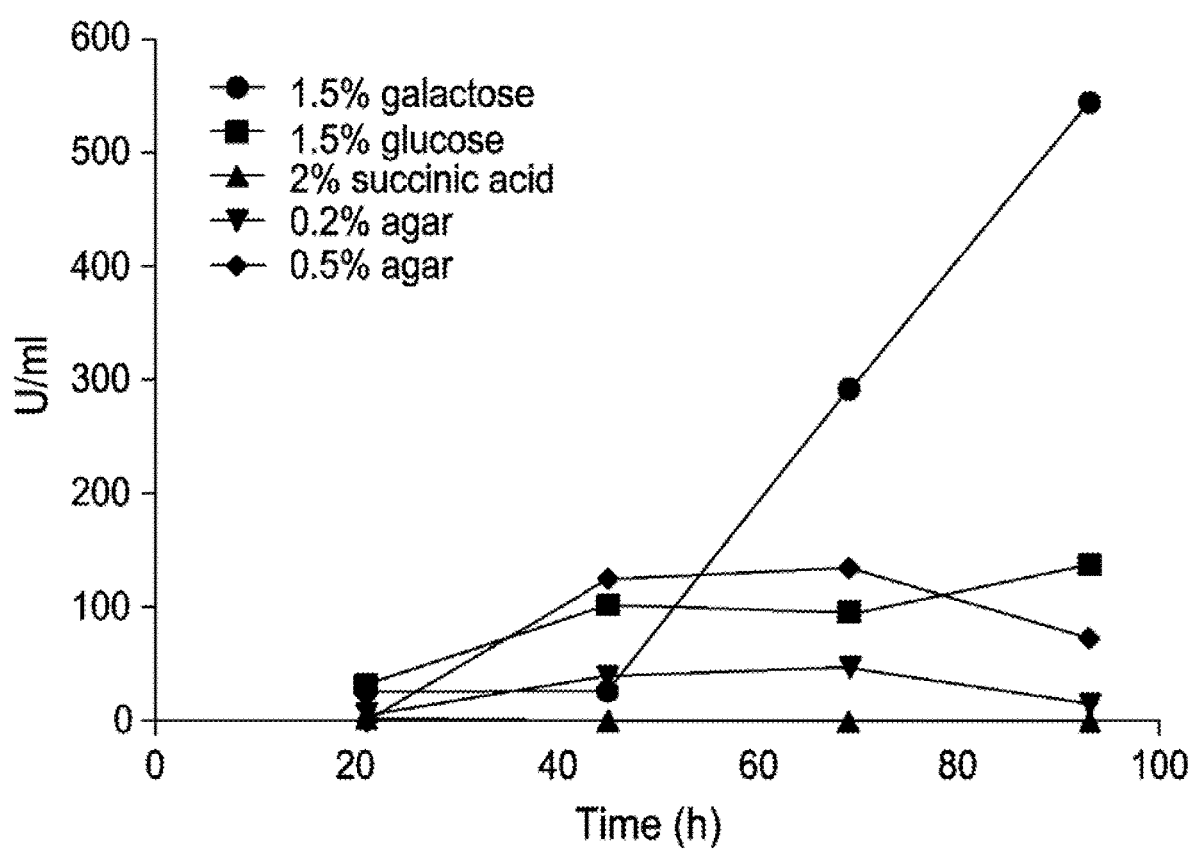

FIG. 8 shows the result of measuring β-agarase activity of *Streptomyces coelicolor* A3(2)_M22-2C43 strain culture fluid based on the type of carbon source in the culture medium by a reducing sugar quantitative assay method.

Figure 9:
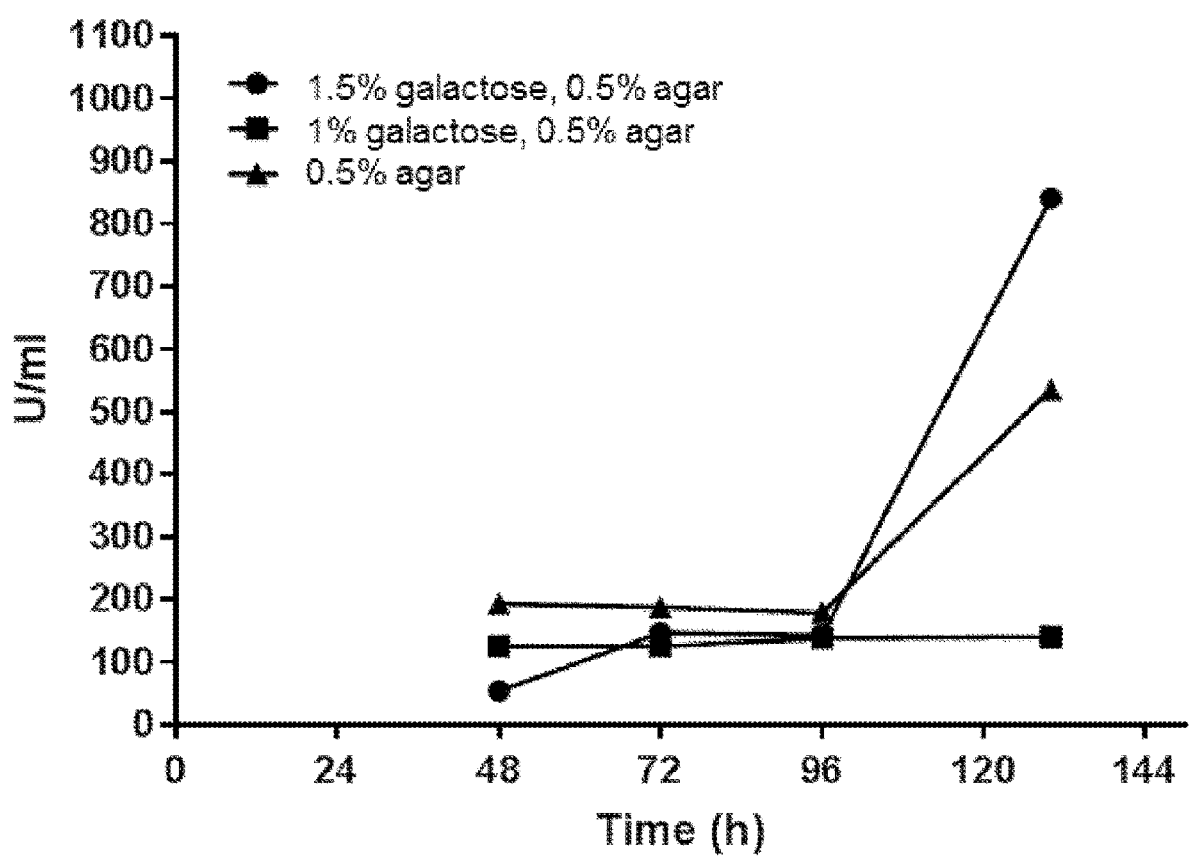

FIG. 9 shows the result of measurement of the β-agarase activity of the culture fluid when *Streptomyces coelicolor* A3(2)_M22-2C43 strain is cultured in a culture medium containing carbon sources under the temperature condition at 28° C. and the shaking condition at 216 rpm, using a reducing sugar quantitative assay method.

Figure 10:
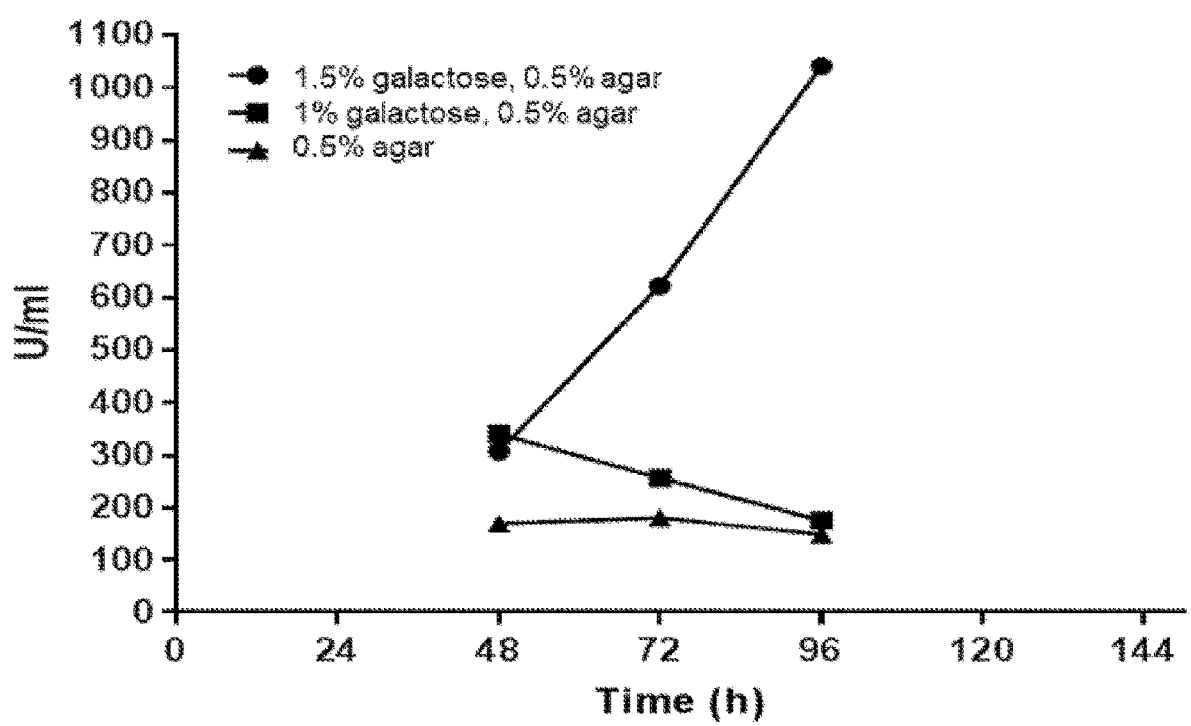

FIG. 10 shows the result of measurement of the β-agarase activity of the culture fluid when *Streptomyces coelicolor* A3(2)_M22-2C43 strain is cultured in a culture medium containing carbon sources under the temperature conditions at 30° C. and shaking conditions at 250 rpm, using a reducing sugar quantitative assay method.

DETAILED DESCRIPTION OF EMBODIMENT

Hereinafter, the present disclosure will be described in more detail based on Examples. However, the following Examples are intended to clearly illustrate the technical characteristics of the present disclosure, and do not limit the scope of protection of the present disclosure.

1. Method for Measuring Enzymic Activity (1) Measurement of β-Agarase Activity of Sample The β-agarase activity of the sample was measured using the reducing sugar quantitative method (DNS method). Specifically, 490 μl of a 20 mM Tris-HCl solution (pH 7) in which agarose was dissolved at a concentration of 0.5% (w/v) was mixed with 10 μl of sample and the mixture reacted at 40° C. for 15 minutes. A DNS reagent (prepared by dissolving dinitrosalicylic acid 6.5 g, 2M NaOH 325 ml and glycerol 45 ml in 1 liter of distilled water) in the same amount as that of the reaction solution was added to the reaction solution boil which in turn was boiled for 10 minutes, and then was cooled. An absorbance at 540 nm was measured. The β-agarase activity 1U(Unit) was defined as an activity with an absorbance of 0.001 at 540 nm.

(2) Evaluation of DagA Enzymic Activity of Sample

The *Streptomyces coelicolor* strain produces DagA and DagB enzymes using β-agarase. DagA enzyme is known to degrade agar or agarose to produce mainly DP4 (neoagarotetraose) and DP6 (neoagarohexaose), while DagB enzyme is reported to produce DP2 (neoagarobiose) mainly by decomposing agar or agarose. DagA enzymic activity of the sample was evaluated by reacting agarose with an enzyme in the sample to decompose the same and then analyzing the decomposition product using a thin layer chromatography (TLC) method, and performing qualitative comparison between amounts of DP2 (neoagarobiose), DP4 (neoagarotetraose), and DP6 (neoagarohexaose) contained in the degradation product. Specifically, the β-agarase activity of the sample was adjusted to 250 U/ml, and 1 ml of a 20 mM Tris-HCl solution (pH 7) ion which the agarose was dissolved at a concentration of 0.5% (w/v) was mixed therewith and the mixture was reacted at 40° C. for 16 hr. Thereafter, the reaction solution was boiled for 10 minutes and then centrifuged to collect the supernatant. Thereafter, 5 μl of the supernatant was added dropwise to a TLC silica gel 60 glass plate, and was developed twice with a developing solvent (a mixed solution of butanol, ethanol, and sterile distilled water at a ratio of 5:3:2 (v/v)). A 10% (v/v) sulfuric acid solution (base solvent being ethanol) was sprayed thinly thereto and then reaction occurred at 110° C. for 15 minutes. Thereafter, patterns of degradation products developed on the TLC plates were compared with each other. In one example, a solution in which each of DP2 (neoagarobiose), DP4 (neoagarotetraose), and DP6 (neoagarohexaose) was mixed therewith at a concentration of 30 mg/ml was used as a standard solution. 0.5 μl of the standard solution was dropped on a TLC silica gel 60 glass plate and was developed using the same method as above.

2. Mutation Induction of Actinomyces *Streptomyces Coelicolor* using Ultraviolet (UV) Irradiation and Selection of Mutation Strain Overexpressing β-Agarase (1) Selection of *Streptomyces Coelicolor* A3(2)_M22 strain

*Streptomyces coelicolor* A3(2) wild-type (WT) strain was stationary-cultured for 5 days in actinomyces minimal culture medium (Minimal medium, MM; Hopwood, 1967) on a plate. After dispensing 2 ml of a 20% (w/v) glycerol solution on the plate, spores were collected and used for mutation induction experiments by UV irradiation. 1 μl of *Streptomyces coelicolor* A3(2) spore stock solution was input into a Petri dish, and 10 ml of a tryptic soy broth (TSB) culture medium (containing 17 g of tryptone, 3 g of soytone, 2.5 g of glucose, 5 g of NaCl, and 2.5 g of $K_2HPO_4$) based on 1 liter of distilled water) as a general bacterial nutrient culture medium was added thereto and the solution was diluted to form a thin film. Thereafter, after irradiating 30 W ultraviolet (UV) thereto for 45 minutes at a height of about 30 cm while ambient light was blocked, we collected a culture fluid and incubated the same for 8 hr under 28° C. temperature condition, 180 rpm shaking condition and in the dark condition. The culture fluid was plated on a MM agar culture medium on the plate, and then incubated for 8 days in an incubator at 28° C. under the dark condition. Subsequently, viable colonies were counted on the plate, and were stained using a dyeing reagent (Congo red). 1,581 colonies with a large clear zone size were first selected. 1,400 colonies among the first selected colonies were individually dispensed on a glass filter paper coated with a MM liquid culture medium [containing 2% (w/v) concentration of agarose as a carbon source] and then were subjected to stationary culture at 28° C. for 5 days, and then 313 strains with many spore formations were second selected. The second selected strains were inoculated into a RSM3 liquid culture medium (containing 5 g $MgCl_2.7H_2O$, 11 g yeast extract, and 0.5 g $CaCO_3$ based on 1 liter of distilled water) containing 2% (w/v) concentration of agarooligosaccharide. Then, incubation thereof was carried out for 2.5 days under a temperature condition of 28° C. and a shaking condition of 180 rpm. Subsequently, the culture fluid was centrifuged such that cell debris was removed therefrom, and then the supernatant was collected. Subsequently, the supernatant was sterilized and filtered with a 0.45 μm syringe filter to collect the purified supernatant. Thereafter, the β-agarase activity of the purified supernatant was measured using the reducing sugar quantitative method (DNS method). Further, the parent strain, that is, the *Streptomyces coelicolor* A3(2) wild-type (WT) strain was cultured in the same manner and conditions, and then the β-agarase activity of the purified supernatant thereof was measured. We compared the β-agarase activity of the second selected strains with that of the *Streptomyces coelicolor* A3(2) wild-type (WT) strain. Then, the mutation strain with the highest β-agarase activity was selected as a final strain and was named *Streptomyces coelicolor* A3(2)_M22.

(2) Deposit Information of *Streptomyces Coelicolor* A3(2)_M22 strain

The present inventors deposited the final selected *Streptomyces coelicolor* A3(2)_M22 strain on Jun. 17, 2016 to the Korean Culture Center of Microorganisms, an international depository (Address: 3F, Yurim Building 45, Hongjenae 2-ga-gil, Seodaemun-gu, Seoul, Korea) in a domestic patent application manner. Therefore, an accession number KFCC 11668P was assigned thereto.

3. Mutation Induction of *Streptomyces Coelicolor* A3(2)_M22 strain by UV Irradiation and Selection of Mutation Strains Overexpressing DagA β-Agarase (1) Selection of *Streptomyces Coelicolor* A3(2)_M22-2C43 Strain

*Streptomyces coelicolor* A3(2)_M22 strain as a mutation strain of the *Streptomyces coelicolor* A3(2) wild-type (WT) strain was stationary-cultured for 5 days in an actinomyces complete culture medium (ISP4 medium) on a plate. After dispensing 2 ml of a 20% (w/v) glycerol solution on the plate, spores were collected and used for mutation induction experiments by UV irradiation. 1 μl of *Streptomyces coelicolor* A3(2)_M22 strain spore stock solution was input into a Petri dish, and 5 ml of a tryptic soy broth (TSB) culture medium (containing 17 g of tryptone, 3 g of soytone, 2.5 g of glucose, 5 g ofNaCl, and 2.5 g of $K_2HPO_4$) based on 1 liter of distilled water) as a general bacterial nutrient culture medium was added thereto and the solution was diluted to form a thin film. Thereafter, UV rays (UV) of 30 to 40 W intensity are irradiated thereto for 24 to 60 minutes at a distance of about 35 to 50 cm while ambient light was blocked. The culture fluid was collected and incubated for 8 hr under 28° C. temperature condition, 180 rpm shaking condition and dark condition. The culture fluid was plated on a MM agar culture medium, and then was subjected to stationary culture for 5 days in an incubator at 28° C. under dark condition. Thereafter, viable colonies were counted on the plate. In this connection, a mortality percentage thereof was 99.2%. A clear zone thereof was dyed using a dyeing reagent (Lugol's Iodine). After comparing the sizes thereof with each other, strains of colonies having different morphologies were classified from each other and then were stationary cultured at 28° C. for 5 days in MM agar culture medium on a plate. Thereafter, the selected strains were inoculated in a liquid culture medium (containing 5 g $MgCl_2.7H_2O$, 11 g yeast extract, and 0.5 g $CaCO_3$ based on 1 liter of distilled water) containing 0.5% (w/v) concentration of agarose. Shaking culture thereof was performed for 2.5 days under a temperature condition of 28° C. and a shaking condition of 216 rpm. Subsequently, the culture fluid was centrifuged to remove cell debris and then the supernatant was collected. Subsequently, the supernatant was sterilized and filtered with a 0.45 μm syringe filter to collect the purified supernatant. Thereafter, the β-agarase activity and DagA enzymic activity of the purified supernatant were measured. A mutation strain having the highest β-agarase activity and DagA enzymic activity was selected as a final strain, and was named *Streptomyces coelicolor* A3(2)_M22-2C43.

(2) Deposit Information of *Streptomyces Coelicolor* A3(2)_M22-2C43 Strain

The present inventors deposited the final selected *Streptomyces coelicolor* A3(2)_M22-2C43 strain on Sep. 22, 2017 at the Korean Culture Center of Microorganisms, an international depository (Address: 3F, Yurim Building, 45 Hongjenae 2-ga-gil, Seodaemun-gu, Seoul, Korea) in a domestic patent application manner and then the accession number KFCC 11742P was allocated thereto. Further, the present inventors applied for conversion of the *Streptomyces coelicolor* A3(2)_M22-2C43 strain (accession number: KFCC 11742P) deposited in Korea to an international patent deposit based on the Budapest Treaty on Aug. 23, 2019. Thus, an accession number KCCM 12577P was allocated thereto.

4. Comparison Between *Streptomyces Coelicolor* A3(2) Wild-Type (WT) Strain, *Streptomyces Coelicolor* A3(2)_M22 Strain and *Streptomyces Coelicolor* A3(2)_M22-2C43 Strain (1) Comparison of Colony Morphologies of Respective Strains FIG. 1 is a photograph showing the colony morphology of each of *Streptomyces coelicolor* A3(2) wild-type (WT) strain, *Streptomyces coelicolor* A3(2)_M22 strain, and *Streptomyces coelicolor* A3(2) M22-2C43 strain. A picture in a lower row in FIG. 1 shows the result of staining colonies with a dyeing reagent.

(2) Culture of Each Strain and Preparation of Enzyme Sample Containing β-Agarase Each strain was inoculated in 1000 ml of liquid culture medium (containing 5 g of $MgCl_2.7H_2O$, 11 g of yeast extract, 0.5 g of $CaCO_3$ based on 1 liter of distilled water) containing 0.5% (w/v) concentration of agarose and was subjected to shaking culture at 28° C. temperature condition and a shaking condition of 216 rpm for 2.5 days. Thereafter, the culture fluid was centrifuged to remove cell debris and the supernatant was collected. Using the collected supernatant as a sample, β-agarase activity thereof was measured, and DagA enzymic activity thereof was evaluated. Thereafter, the supernatant was sterilized and filtered with a 0.45 μm syringe filter to collect the purified supernatant. Thereafter, ammonium sulfate was added to the purified supernatant so that the saturation concentration of the protein contained in the supernatant was 50% and 70%, respectively. The β-agarase enzyme was precipitated via ammonium sulfate precipitation (ASP) as a type of a salting out method, and then the purified β-agarase enzyme in the form of a pellet was obtained via centrifugation. According to the contents disclosed in the specification of the patent application of *Streptomyces coelicolor* A3(2)_M22 strain (Korean Patent Application Publication No. 10-2018-0019881, 2018 Feb. 27), it is indirectly identified that when the protein saturation concentration of the ammonium sulfate-added supernatant is 50%, DagA enzyme is mainly precipitated, and when the protein saturation concentration of the ammonium sulfate-added supernatant is 70%, both DagA enzyme and DagB enzyme are precipitated. After dissolving the purified β-agarase enzyme in the form of a pellet in 5 ml of distilled water, the β-agarase activity thereof was measured, and DagA enzymic activity thereof was evaluated.

(3) Comparison of β-Agarase Activities of Enzyme Samples Obtained from Respective Strains Table 1 below shows a measurement result of the β-agarase activity each of supernatant samples obtained through culture of *Streptomyces coelicolor* A3(2) wild-type (WT) strain, *Streptomyces coelicolor* A3(2)_M22 strain and *Streptomyces coelicolor* A3(2)_M22-2C43 strain, a 50% ASP sample (an enzyme sample obtained by adding ammonium sulfate so that the saturation concentration of the protein contained in the supernatant becomes 50%), and a 70% ASP sample (an enzyme sample obtained by adding ammonium sulfate so that the saturation concentration of the protein contained in the supernatant becomes 70%). A unit of the β-agarase activity is U/ml.

TABLE 1

| Samples | *S. coelicolor* A3(2) WT | *S. coelicolor* A3(2)_M22 | *S. coelicolor* A3(2)_M22-2C43 |
|---|---|---|---|
| Supernatant | 799 | 1,163 | 1,133 |
| 50% ASP | 2,150 | 15,875 | 23,155 |
| 70% ASP | 20,875 | 35,119 | 32,524 |

As shown in Table 1 above, regarding the 50% ASP sample expected to be composed mainly of DagA enzyme, 50% ASP sample obtained from the culture fluid of the *Streptomyces coelicolor* A3(2)_M22-2C43 strain exhibited the highest β-agarase activity.

(4) Comparison Between DagA Enzymic Activities of Enzyme Samples Obtained from Respective Strains FIG. 2 shows analysis results of the DagA enzymic activity of each of supernatant samples obtained through culture of *Streptomyces coelicolor* A3(2) wild-type (WT) strain, *Streptomyces coelicolor* A3(2)_M22 strain and *Streptomyces coelicolor* A3(2)_M22-2C43 strain, a 50% ASP sample (an enzyme sample obtained by adding ammonium sulfate so that the saturation concentration of the protein contained in the supernatant becomes 50%), and a 70% ASP sample (an enzyme sample obtained by adding ammonium sulfate so that the saturation concentration of the protein contained in the supernatant is 70%) using a thin layer chromatography (TLC) method. In FIG. 2, 'M' represents the standard solution, all of lanes '1', '4' and '7' denote enzyme samples obtained from the culture fluid of *Streptomyces coelicolor* A3(2) wild-type (WT) strain, and all of lanes '2', '5' and '8' denote samples obtained from the culture fluid of *Streptomyces coelicolor* A3(2)_M22 strain. All of lanes '3', '6' and '9' denote samples obtained from the culture fluid of *Streptomyces coelicolor* A3(2)_M22-2C43 strain. Further, all of lane '1', '2' and '3' are all supernatant samples, all of lanes '4', '5' and '6' are 70% ASP samples, and all of lanes '7', '8' and '9' are 50% ASP samples.

As shown in FIG. 2, all of the enzyme samples obtained from the culture fluid of *Streptomyces coelicolor* A3(2)_M22-2C43 strain decomposed agarose regardless of the level of separation and purification, thereby producing mainly DP4 (neoagarotetraose) and DP6 (neoagarohexaose). To the contrary, the supernatant sample and the 70% ASP sample as obtained from the culture fluid of *Streptomyces coelicolor* A3(2)_M22 strain decomposed agarose to produce mainly DP2 (neoagarobiose).

FIG. 3 shows an analyzing result of a composition of neo-agarosaccharide in a degradation product using HPLC-ELSD, wherein the degradation product is obtained by reacting agarose with a 70% ASP sample obtained through culture of *Streptomyces coelicolor* A3(2)_M22-2C43 strain. The decomposition reaction conditions of agarose are the same as those used in the DagA enzymic activity evaluation. The agarose decomposition reaction was repeated a total of 4 times under the same condition. When analyzing the composition of the neo-agarosaccharide in the decomposition product using HPLC-ELSD, an NH2 P-50 4E multimode column (250 mm×4.6 mm) was used as a column, and a mixed solution of acetonitrile and water (mixing ration of acetonitrile:water being 65:35 based on weight) was used as a mobile phase. As shown in FIG. 3, a content of DP4 (neoagarotetraose) in the decomposition product of agarose is 5 to 5.5 times larger than that of DP2 (neoagarobiose). A content of DP6 (neoagarohexaose) was found to be 3 to 3.5 times larger than that of DP2 (neoagarobiose).

(5) β-Agarase Gene Information of Each Strain

We amplified the DagA gene and DagB gene of each of *Streptomyces coelicolor* A3(2) wild-type (WT) strain, *Streptomyces coelicolor* A3(2)_M22 strain and *Streptomyces coelicolor* A3(2)_M22-2C43 strain using a PCR reaction. The DNA base sequence of the amplified PCR product was analyzed. The DagB genes of the *Streptomyces coelicolor* A3(2) wild-type (WT) strain and the *Streptomyces coelicolor* A3(2)_M22 strain were found to have the same base sequence represented by SEQ ID NO:1. To the contrary, the DagB gene of the *Streptomyces coelicolor* A3(2)_M22-2C43 strain was modified via gene mutation as a substitution, and was found to have the base sequence represented by SEQ ID NO:2. FIG. 4 shows some of comparison results of the DagB gene base sequence (upper line) of the *Streptomyces coelicolor* A3(2) wild-type (WT) strain and the DagB gene base sequence (lower line) of the *Streptomyces coelicolor* A3(2)_M22-2C43 strain as aligned with each other. In one example, all of the DagA genes of *Streptomyces coelicolor* A3(2) wild-type (WT) strain, *Streptomyces coelicolor* A3(2)_M22 strain and *Streptomyces coelicolor* A3(2)_M22-2C43 strain were found to have the same base sequence represented by SEQ ID NO:3. Therefore, all of *Streptomyces coelicolor* A3(2) wild-type (WT) strain, *Streptomyces coelicolor* A3(2)_M22 strain, and *Streptomyces coelicolor* A3(2)_M22-2C43 strain are expected to express the DagA enzyme having the amino acid sequence represented by SEQ ID NO:4. Further, *Streptomyces coelicolor* A3(2) wild-type (WT) strain and *Streptomyces coelicolor* A3(2)_M22 strain are predicted to express a normal DagB enzyme having the amino acid sequence represented by SEQ ID NO:5. To the contrary, *Streptomyces coelicolor* A3(2)_M22-2C43 strain is predicted not to express the normal DagB enzyme but to express DagB mutant enzyme with amino acid sequence represented by SEQ ID NO:6 and little β-agarase activity.

(6) Lineage and Relationship of *Streptomyces Coelicolor* A3(2)_M22-2C43 Strain

The 16S rRNA base sequence of the *Streptomyces coelicolor* A3(2) wild-type (WT) strain and the 16S rRNA base sequence of the *Streptomyces coelicolor* A3(2)_M22-2C43 strain were analyzed using colony PCR. FIG. 5 shows the biological lineage and relationship of the *Streptomyces coelicolor* A3(2)_M22-2C43 strain prepared based on the 16S rRNA base sequence.

(7) Comparison Between Expression Levels by DagB Genes

The DagB gene of the *Streptomyces coelicolor* A3(2) wild-type (WT) strain was cloned into the pUWL201pw vector with the cleavage map in FIG. 6 to create a recombinant vector thereof *Streptomyces lividans* TK24 strain which does not have a β-agarase gene was transformed using the recombinant vector to prepare a recombinant strain WT dagB. Further, a recombinant vector was produced by cloning the DagB gene of the *Streptomyces coelicolor* A3(2)_22-2C43 strain into the pUWL201pw vector. *Streptomyces lividans* TK24 strain was transformed using the recombinant vector to prepare a recombinant strain M22-2C43 dagB. Further, a recombinant strain pUWL201pw was prepared by transforming the *Streptomyces lividans* TK24 strain using the pUWL201pw vector. Thereafter, the three recombinant strains were cultured, and culture fluids thereof were collected on first, second, and third days during the culturing, and the supernatants thereof were obtained. Thereafter, the β-agarase activity of the supernatant sample was measured using the reducing sugar quantitative assay method (DNS method). FIG. 7 shows the β-agarase activity of each of supernatants obtained from culture of recombinant strain WT dagB, recombinant strain M22-2C43 dagB and recombinant strain pUWL201pw prepared in the examples of the present disclosure based on the culture date. As shown in FIG. 7, the DagB gene of the *Streptomyces coelicolor* A3(2) wild-type (WT) strain was expressed at a high level using a normal DagB enzyme with β-agarase activity. To the contrary, the modified DagB gene of the *Streptomyces coelicolor* A3(2)_M22-2C43 strain was not expressed using the normal DagB enzyme or was expressed using the DagB mutant enzyme with little β-agarase activity.

5. Establishment of Optimal Culture Conditions for β-Agarase of *Streptomyces Coelicolor* A3(2)_M22-2C43 Strain (1) Type and Content of Carbon Source in Culture Medium

*Streptomyces coelicolor* A3(2)_M22-2C43 strain was cultured for 4 days in an actinomyces agar culture medium containing agar at a 1.5 wt % concentration as a carbon source. Thereafter, 3 strain colonies, each having a size of 1 cm×1 cm, were inoculate into 50 ml of a RSM3 liquid culture medium containing one selected from 1.5% (w/v) concentration of galactose, 2% (w/v) concentration of succinic acid, 1.5% (w/v) concentration of glucose, agar of 0.2% (w/v) concentration and agar of 0.5% (w/v) concentration as a carbon source, and then were incubated for 2.5 days under a temperature condition of 28° C. and a shaking condition of 216 rpm. Thereafter, the supernatant was collected from the culture fluid and the activity of the β-agarase contained in the supernatant was measured.

FIG. 8 shows the result of measuring β-agarase activity of *Streptomyces coelicolor* A3(2)_M22-2C43 strain culture fluid based on the type of carbon source in the culture medium by a reducing sugar quantitative assay method. In FIG. 8, the Y-axis represents the β-agarase activity and the X-axis represents the culturing duration. Table 2 below shows the β-agarase activity of the culture fluid based on the type of carbon source in the culture medium when the *Streptomyces coelicolor* A3(2)_M22-2C43 strain was cultured for 96 hr.

TABLE 2

| Carbon source | 1.5%(w/v) galactose | 1.5%(w/v) glucose | 2%(w/v) succinic acid | 0.2%(w/v) agar | 0.5%(w/v) agar |
|---|---|---|---|---|---|
| β-agarase activity(U/ml) | 546 | 137 | 0 | 15 | 72.5 |

As shown in FIG. 8 and Table 2 above, it is identified that the carbon source in the culture medium for optimal production of β-agarase from the *Streptomyces coelicolor* A3(2)_M22-2C43 strain is galactose, and a concentration thereof is 1.5% (w/v).

(2) Culture Temperature and Culturing Agitation Speed (rpm) 3 strain colonies, each having 1 cm×1 cm size were inoculated into each of 50 ml of RSM3 liquid culture medium containing 1% (w/v) concentration of galactose and 0.5% (w/v) concentration of agar as a carbon source, 50 ml of RSM3 liquid culture medium containing 1.5% (w/v) concentration of galactose and 0.5% (w/v) concentration of agar as a carbon source, and 50 ml of RSM3 liquid culture medium containing 0.5% (w/v) concentration of agar as a carbon source. Then, incubation thereof was performed for 2.5 days under a temperature condition of 28° C. and shaking condition of 216 rpm or under a temperature condition of 30° C. and a shaking condition of 250 rpm. Thereafter, a supernatant was collected from a culture fluid and then the activity of β-agarase contained in supernatant was measured.

FIG. 9 shows the result of measurement of the β-agarase activity of the culture fluid when *Streptomyces coelicolor* A3(2)_M22-2C43 strain is cultured in a culture medium containing carbon sources under the temperature condition at 28° C. and the shaking condition at 216 rpm, using a reducing sugar quantitative assay method. FIG. 10 shows the result of measurement of the β-agarase activity of the culture fluid when *Streptomyces coelicolor* A3(2)_M22-2C43 strain is cultured in a culture medium containing carbon sources under the temperature conditions at 30° C. and shaking conditions at 250 rpm, using a reducing sugar quantitative assay method. In FIG. 9 and FIG. 10, the Y-axis represents the β-agarase activity and the X-axis represents the culturing duration. As shown in FIG. 9 and FIG. 10, it is identified that the culture conditions for optimal production of β-agarase during culture of the *Streptomyces coelicolor* A3(2)_M22-2C43 strain are a temperature of 30° C. and shaking (stirring speed) at 250 rpm.

As described above, the present disclosure has been described based on the above examples. However, the present disclosure is not necessarily limited thereto, and various modifications may be implemented within the scope and spirit of the present disclosure. Therefore, the scope of protection of the present disclosure should be construed as including all embodiments belonging to the scope of the claims attached to the present disclosure.

[Accession Number]
Depositary Organization Name: Korean Culture Center of Microorganisms
Accession number: KFCC 11668P
Deposit Date: 2016 Jun. 17
[Accession Number]
Depositary Organization Name: Korean Culture Center of Microorganisms
Accession number: KFCC 11742P
Deposit Date: 2017 Sep. 22
[Accession Number]
Depositary Organization Name: Korean Culture Center of Microorganisms
Accession number: KCCM 12577P
Deposit date: 2019 Aug. 23

The invention claimed is:

1. A *Streptomyces coelicolor* A3(2)_M22-2C43 strain having the accession number KCCM 12577P.

2. A method for producing β-agarase, the method comprising:
    (a) inoculating and culturing the *Streptomyces coelicolor* A3(2)_M22-2C43 strain having the accession number KCCM 12577P of claim 1 into a liquid culture medium containing galactose as a carbon source, thereby obtaining a culture fluid; and
    (b) centrifuging the culture fluid to obtain a supernatant.

3. The method of claim 2, wherein a concentration of galactose in the liquid culture medium is 0.5% (w/v) to 4% (w/v).

4. The method of claim 2, wherein a culture temperature of the *Streptomyces coelicolor* A3(2)_M22-2C43 strain having the accession number KCCM 12577P is 25 to 35° C. and a culturing agitation speed thereof is 200 to 300 rpm.

5. The method of claim 2, wherein a culturing duration of the *Streptomyces coelicolor* A3(2)_M22-2C43 strain having the accession number KCCM 12577P is 40 to 150 hr.

6. A method for producing β-agarase, the method comprising:
(a) inoculating and culturing the *Streptomyces coelicolor* A3(2)_M22-2C43 strain having the accession number KCCM 12577P of claim 1 into a liquid culture medium containing galactose as a carbon source, thereby obtaining a culture fluid;
(b) centrifuging the culture fluid to obtain a supernatant; and
(c) precipitating the β-agarase contained in the supernatant by adding ammonium sulfate to the supernatant.

7. The method of claim 6, wherein the ammonium sulfate is added so that a protein saturation concentration of the supernatant is 45% to 70%.

8. A neoagarooligosaccharide preparation method comprising:
(a') preparing a culture fluid of the *Streptomyces coelicolor* A3(2)_M22-2C43 strain having the accession number KCCM 12577P of claim 1 or a supernatant of the culture fluid; and
(b') performing enzymatic reaction of agar or agarose with β-agarase present in the culture fluid or the supernatant.

\* \* \* \* \*

SEQUENCE LISTING

<160> NUMBER OF SEQ ID NOS: 6

<210> SEQ ID NO 1
<211> LENGTH: 2397
<212> TYPE: DNA
<213> ORGANISM: Unknown
<220> FEATURE:
<223> OTHER INFORMATION: DagB gene derived from Streptomyces coelicolor A3(2)

<400> SEQUENCE: 1

| | | | | | | |
|---|---|---|---|---|---|---|
| atgaccgtgc | acaagcgcgc | ttgcaccact | ccgccgccgc | gagccagcag | gtcgttccgc | 60 |
| gtgaggtggc | ctgtcctgat | agcggccgcc | tgcgccgggt | tagtcctggc | gaccaccagc | 120 |
| cctccggccg | tcgcggccgg | cgctcatgac | ctcggcgacg | agaccatgct | ctacgacttc | 180 |
| caggacggcc | tggtaccggc | cgaggtcggc | ccgtaccagg | cgaagacgac | aatcgtcggt | 240 |
| cgcggcgaca | agaagctccg | ggtcgatttc | caggcccgga | agaactacta | ctcctcgttc | 300 |
| tccgtacgcc | ccgagcccgt | gtggaactgg | tcggcggagg | agtccgagtc | gctcggcatc | 360 |
| gcgatggagc | tcacgaaccc | gagcgaccgc | tccgtccagc | tcacgatcga | tctggagagc | 420 |
| tcgaccggcg | tcgccacccg | cagtgtcaac | gtcccggccg | gcggcggtgg | cacgtactac | 480 |
| ttcgacgtcg | acagcccgc | gctccaccgc | gacaccgggc | tgcgcgccga | tccgtcctgg | 540 |
| ctcgcggaca | aggacgtcac | ctctgcggtc | tggatgtggg | gctccaagga | gacggacacg | 600 |
| agccgcatca | gccagctgaa | cttctacgtc | gccggcctgc | tgcacgaccg | gtcggtcatc | 660 |
| gtggacgaca | tccgcgtcgt | ccgtgacgcg | ccggcagacc | ccgattacct | caagggcctg | 720 |
| gtcgacgcct | tcggtcagaa | caacaaggtc | gactacaagg | gaaaggtctc | caggacgtcg | 780 |
| gagattcttc | ggcagcgcgc | tgccgaagcc | aaggaccttc | gcaggcatcc | ggttccggag | 840 |
| gaccggtcca | ggtacggcgg | ctggctgaac | ggtccacgac | tcgaggcgac | gggcaacttc | 900 |
| cgcgtggaga | agtaccaggg | gcggtggacc | ctggtggacc | ctgacggcta | cctgttcttc | 960 |
| tcaaccggca | tcgacaacgc | ccgcatgttc | gactccccaa | ccacgacggg | ttacgacttc | 1020 |
| gaccatgacg | cgatccagga | gctgccgccc | ccagcctga | cggccggcgg | ccccgaggac | 1080 |
| ctcaaccgcg | tccagaagtc | ggcgctgccg | acccgcacga | agatgtccga | aacccgcgcc | 1140 |
| gacctcttca | gcaagttgcc | caagtaccgc | acccgcgcgg | gcgagggctt | cggttacgcc | 1200 |
| cccgacaccc | tggccggtcc | cgtcgcgcag | ggcgagacct | acagcttcta | caaggcgaac | 1260 |
| gtcgcccgga | agtaccccgg | cagcaactac | atggagcggt | ggcgggacaa | cacggtcgac | 1320 |
| cggatgctca | gctggggctt | cacctccttc | ggcaactgga | ccgacccgga | gatgtacgac | 1380 |
| aacgaccgta | tcccgtactt | cgcccacggc | tggatcaagg | gcgacttcaa | gacggtgagc | 1440 |
| accggccagg | actactgggg | cccgatgccg | gacccgttcg | accccgcgtt | ctccgacgcc | 1500 |
| gcagccagaa | ccgcgcgagc | agtcgccgac | gaggtcgcgg | acagcccgtt | ggcgatcggc | 1560 |
| gtattcatgg | acaacgaact | gagctggggc | aacgccggca | gtttcagcac | ccgttacggc | 1620 |
| gtcgtcatcg | acaccatgtc | acgtgacgcg | gcagagagcc | ccaccaagtc | ggcgttctcc | 1680 |
| gacgaactgg | aggagaagta | cgggaccatc | gacgctctca | cgccgcgtg | gcagacgaca | 1740 |
| gttccgtcat | gggaggcact | ccgtagcggc | agtgccgacc | tcggctccga | cgagaccgcg | 1800 |
| aaggagtccg | actactccgc | gctcatgacg | ctctacgcca | ctcagtactt | caagacggtc | 1860 |
| gacgccgagc | tcgacaaggt | catgccggac | catctctacg | cgggttcgag | gttcgccagc | 1920 |
| tggggccgca | caccggaggt | cgtcgaggca | gcgagcaagt | acgtcgacat | catgagctac | 1980 |

```
aacgagtacc gcgagggact gcacccgagc gagtgggcgt ttctcgaaga gctcgacaag    2040
cccagcctca tcggtgagtt ccacatggga acgaccacta ccgggcagcc gcatccgggt    2100
ctcgtctcgg cgggaacgca ggccgagcgg gcacggatgt acgccgagta catggaacag    2160
ctcatcgaca acccgtacat ggtgggcggc cactggttcc agtatgccga ctcgcccgtg    2220
actggcagag cactcgacgg ggagaactac aacattggct tcgtctccgt cacggaccgt    2280
ccctacccgg agatcgtcgc cgctgcccgc gacgtgaacc agcgtctcta tgaccgccga    2340
tacggcaacc tggccacggc cgagggacat acaccggtc ggcgttcagc ggagtag       2397
```

<210> SEQ ID NO 2
<211> LENGTH: 2397
<212> TYPE: DNA
<213> ORGANISM: Unknown
<220> FEATURE:
<223> OTHER INFORMATION: DagB gene derived from Streptomyces coelicolor
    A3(2)_M22-2C43

<400> SEQUENCE: 2

```
atgaccgtgc acaagcgcgc ttgcaccact ccgccgccgc gagccagcag gtcgttccgc      60
gtgaggtggc ctgtcctgat agcggccgcc tgcgccgggt tagtcctggc gaccaccagc     120
cctccggccg tcgcggccgg cgctcatgac ctcggcgacg agaccatgct ctacgacttc     180
caggacggct tggtaccggc cgaggtcggc ccgtaccagg cgaagacgac aatcgtcggt     240
cgcggcgaca agaagctccg ggtcgatttc caggcccgga gaactacta ctcctcgttc     300 tccgtacgcc ccgagcccgt gtggaactgg tcggcggagg agtccgagtc gctcggcatc     360
gcgatggagc tcacgaaccc gagcgaccgc tccgtccagc tcacgatcga tctggagagc     420
tcgaccggcg tcgccacccg cagtgtcaac gtcccggccg gcggcggtgg cacgtactac     480
ttcgacgtcg acagccccgc gctccaccgc gacaccgggc tgcgcgccga tcgtcctgg     540 ctcgcggaca aggacgtcac ctctgcggtc tggatgtggg ctccaaggca gacggacacg     600
agccgcatca gccagctgaa cttctacgtc gccggcctgc tgcacgaccg gtcggtcatc     660
gtggacgaca tccgcgtcgt ccgtgacgcg ccggcagacc ccgattacct caagggcctg     720
gtcgacgcct tcggtcagaa caacaaggtc gactacaagg gaaaggtctc caggacgtcg     780
gagattcttc ggcagcgcgc tgccgaagcc aaggaccttc gcaggcatcc ggttccggag     840
gaccggtcca ggtacggcgg ctggctgaac ggtccacgac tcgaggcgac gggcaacttc     900
cgcgtggaga gtaccaggg gcggtggacc ctggtggacc ctgacggcta cctgttcttc     960
tcaaccggca tcgacaacgc ccgcatgttc gactccccaa ccacgacggg ttacgacttc    1020
gaccatgacg cgatccagga gctgccgccc ccagcctga cggccggcgg ccccgaggac    1080
ctcaaccgcg tccagaagtc ggcgctgccg accgcacga agatgtccga aacccgcgcc    1140
gacctcttca gcaagttgcc caagtaccgc acccgcgcgg gcgagggctt cggttacgcc    1200
cccgacaccc tggccggtcc cgtcgcgcag ggcgagacct acagcttcta caaggcgaac    1260
gtcgcccgga agtaccccgg cagcaactac atggagcggt ggcgggacaa cacggtcgac    1320
cggatgctca gctggggctt cacctccttc ggcaactgga ccgacccgga gatgtacgac    1380
aacgaccgta tcccgtactt cgcccacggc tggatcaagc gcgacttcaa gacggtgagc    1440
accggccagg actactgggg cccgatgccg gacccgttcg acccgcgtt ctccgacgcc    1500 gcagccagaa ccgcgcgagc agtcgccgac gaggtcgcgg acagcccgtt ggcgatcggc    1560
gtattcatgg acaacgaact gagctggggc aacgccggca gtttcagcac ccgttacggc    1620
```

| | |
|---|---|
| gtcgtcatcg acaccatgtc acgtgacgcg gcagagagcc ccaccaagtc ggcgttctcc | 1680 |
| gacgaactgg aggagaagta cgggaccatc gacgctctca acgccgcgtg gcagacgaca | 1740 |
| gttccgtcat gggaggcact ccgtagcggc agtgccgacc tcggctccga cgagaccgcg | 1800 |
| aaggagtccg actactccgc gctcatgacg ctctacgcca ctcagtactt caagacggtc | 1860 |
| gacgccgagc tcgacaaggt catgccggac catctctacg cgggttcgag gttcgccagc | 1920 |
| tggggccgca caccggaggt cgtcgaggca gcgagcaagt acgtcgacat catgagctac | 1980 |
| aacgagtacc gcgagggact gcacccgagc gagtgggcgt ttctcgaaga gctcgacaag | 2040 |
| cccagcctca tcggtgagtt ccacatggga acgaccacta ccgggcagcc gcatccgggt | 2100 |
| ctcgtctcgg cgggaacgca ggccgagcgg gcacggatgt acgccgagta catggaacag | 2160 |
| ctcatcgaca acccgtacat ggtgggcggc cactggttcc agtatgccga ctcgcccgtg | 2220 |
| actggcagag cactcgacgg ggagaactac aacattggct tcgtctccgt cacggaccgt | 2280 |
| ccctacccgg agatcgtcgc cgctgcccgc gacgtgaacc agcgtctcta tgaccgccga | 2340 |
| tacggcaacc tggccacggc cgagggacat tacaccggtc ggcgttcagc ggagtag | 2397 |

<210> SEQ ID NO 3
<211> LENGTH: 930
<212> TYPE: DNA
<213> ORGANISM: Unknown
<220> FEATURE:
<223> OTHER INFORMATION: DagA gene derived from Streptomyces coelicolor
     A3(2)

<400> SEQUENCE: 3

| | |
|---|---|
| gtggtcaacc gacgtgatct catcaagtgg agtgccgtcg cactcggagc gggtgcgggg | 60 |
| ctcgcgggtc ccgcacccgc cgctcatgcc gcagacctcg aatgggaaca gtaccccgtg | 120 |
| ccggccgccc ctggcggaaa caggtcctgg cagcttctcc ccagccattc ggacgacttc | 180 |
| aactacaccg gcaagcctca aaccttcagg ggcagatggc tggaccagca caaggatggc | 240 |
| tggtcgggcc cggccaacag cctctacagt gcgcgccatt cctgggtggc tgacggaaat | 300 |
| ctcatcgtcg agggccgcag ggcgccggac gggagggtct actgcggcta cgtgacctcc | 360 |
| cgcaccccag tcgagtaccc tctctatacc gaagtactca tgcgtgtgag cgggctgaag | 420 |
| ctctcatcga atttctggct cctgagcaga gacgacgtca acgagattga cgtgatcgaa | 480 |
| tgctacggca acgagtcatt gcacggaaag cacatgaaca ccgcctacca catattccag | 540 |
| cggaacccct tcactgaact ggcgagaagc cagaagggt atttcgcaga tgggagctac | 600 |
| gggtacaatg gtgagactgg gcaggtgttt gggacggcg ccgggcaacc tcttcttcgg | 660 |
| aatggattcc accgctacgg cgtgcactgg ataagcgcca ccgaattcga tttctacttc | 720 |
| aacggcaggt tggtgcgccg gctgaaccgg tcgaacgacc tcagggaccc ccggagccgg | 780 |
| ttcttcgacc agccaatgca tctgatcctc aacaccgaga gtcatcagtg gcgcgtcgac | 840 |
| cgaggtatcg aacccacgga gcggaactc gcagaccca gcatcaacaa catctactac | 900 |
| cgctgggtca ggacgtatca ggccgtgtag | 930 |

<210> SEQ ID NO 4
<211> LENGTH: 309
<212> TYPE: PRT
<213> ORGANISM: Unknown
<220> FEATURE:
<223> OTHER INFORMATION: DagA derived from Streptomyces coelicolor A3(2)

<400> SEQUENCE: 4

```
Met Val Asn Arg Arg Asp Leu Ile Lys Trp Ser Ala Val Ala Leu Gly
1               5                   10                  15

Ala Gly Ala Gly Leu Ala Gly Pro Ala Pro Ala His Ala Ala Asp
            20                  25                  30

Leu Glu Trp Glu Gln Tyr Pro Val Pro Ala Ala Pro Gly Gly Asn Arg
            35                  40                  45

Ser Trp Gln Leu Leu Pro Ser His Ser Asp Asp Phe Asn Tyr Thr Gly
50                  55                  60

Lys Pro Gln Thr Phe Arg Gly Arg Trp Leu Asp Gln His Lys Asp Gly
65                  70                  75                  80

Trp Ser Gly Pro Ala Asn Ser Leu Tyr Ser Ala Arg His Ser Trp Val
            85                  90                  95

Ala Asp Gly Asn Leu Ile Val Glu Gly Arg Arg Ala Pro Asp Gly Arg
            100                 105                 110

Val Tyr Cys Gly Tyr Val Thr Ser Arg Thr Pro Val Glu Tyr Pro Leu
            115                 120                 125

Tyr Thr Glu Val Leu Met Arg Val Ser Gly Leu Lys Leu Ser Ser Asn
            130                 135                 140

Phe Trp Leu Leu Ser Arg Asp Asp Val Asn Glu Ile Asp Val Ile Glu
145                 150                 155                 160

Cys Tyr Gly Asn Glu Ser Leu His Gly Lys His Met Asn Thr Ala Tyr
            165                 170                 175

His Ile Phe Gln Arg Asn Pro Phe Thr Glu Leu Ala Arg Ser Gln Lys
            180                 185                 190

Gly Tyr Phe Ala Asp Gly Ser Tyr Gly Tyr Asn Gly Glu Thr Gly Gln
            195                 200                 205

Val Phe Gly Asp Gly Ala Gly Gln Pro Leu Leu Arg Asn Gly Phe His
            210                 215                 220

Arg Tyr Gly Val His Trp Ile Ser Ala Thr Glu Phe Asp Phe Tyr Phe
225                 230                 235                 240

Asn Gly Arg Leu Val Arg Arg Leu Asn Arg Ser Asn Asp Leu Arg Asp
            245                 250                 255

Pro Arg Ser Arg Phe Phe Asp Gln Pro Met His Leu Ile Leu Asn Thr
            260                 265                 270

Glu Ser His Gln Trp Arg Val Asp Arg Gly Ile Glu Pro Thr Asp Ala
            275                 280                 285

Glu Leu Ala Asp Pro Ser Ile Asn Asn Ile Tyr Tyr Arg Trp Val Arg
            290                 295                 300

Thr Tyr Gln Ala Val
305

<210> SEQ ID NO 5
<211> LENGTH: 798
<212> TYPE: PRT
<213> ORGANISM: Unknown
<220> FEATURE:
<223> OTHER INFORMATION: DagB derived from Streptomyces coelicolor A3(2)

<400> SEQUENCE: 5

Met Thr Val His Lys Arg Ala Cys Thr Thr Pro Pro Arg Ala Ser
1               5                   10                  15

Arg Ser Phe Arg Val Arg Trp Pro Val Leu Ile Ala Ala Cys Ala
            20                  25                  30

Gly Leu Val Leu Ala Thr Thr Ser Pro Pro Ala Val Ala Ala Gly Ala
            35                  40                  45
```

```
His Asp Leu Gly Asp Glu Thr Met Leu Tyr Asp Phe Gln Asp Gly Leu
    50                  55                  60
Val Pro Ala Glu Val Gly Pro Tyr Gln Ala Lys Thr Thr Ile Val Gly
65                  70                  75                  80
Arg Gly Asp Lys Lys Leu Arg Val Asp Phe Gln Ala Arg Lys Asn Tyr
                85                  90                  95
Tyr Ser Ser Phe Ser Val Arg Pro Glu Pro Val Trp Asn Trp Ser Ala
            100                 105                 110
Glu Glu Ser Glu Ser Leu Gly Ile Ala Met Glu Leu Thr Asn Pro Ser
        115                 120                 125
Asp Arg Ser Val Gln Leu Thr Ile Asp Leu Ser Ser Thr Gly Val
    130                 135                 140
Ala Thr Arg Ser Val Asn Val Pro Ala Gly Gly Gly Thr Tyr Tyr
145                 150                 155                 160
Phe Asp Val Asp Ser Pro Ala Leu His Arg Asp Thr Gly Leu Arg Ala
                165                 170                 175
Asp Pro Ser Trp Leu Ala Asp Lys Asp Val Thr Ser Ala Val Trp Met
            180                 185                 190
Trp Gly Ser Lys Glu Thr Asp Thr Ser Arg Ile Ser Gln Leu Asn Phe
        195                 200                 205
Tyr Val Ala Gly Leu Leu His Asp Arg Ser Val Ile Val Asp Asp Ile
    210                 215                 220
Arg Val Val Arg Asp Ala Pro Ala Asp Pro Asp Tyr Leu Lys Gly Leu
225                 230                 235                 240
Val Asp Ala Phe Gly Gln Asn Asn Lys Val Asp Tyr Lys Gly Lys Val
                245                 250                 255
Ser Arg Thr Ser Glu Ile Leu Arg Gln Arg Ala Ala Glu Ala Lys Asp
            260                 265                 270
Leu Arg Arg His Pro Val Pro Glu Asp Arg Ser Arg Tyr Gly Gly Trp
        275                 280                 285
Leu Asn Gly Pro Arg Leu Glu Ala Thr Gly Asn Phe Arg Val Glu Lys
    290                 295                 300
Tyr Gln Gly Arg Trp Thr Leu Val Asp Pro Asp Gly Tyr Leu Phe Phe
305                 310                 315                 320
Ser Thr Gly Ile Asp Asn Ala Arg Met Phe Asp Ser Pro Thr Thr Thr
                325                 330                 335
Gly Tyr Asp Phe Asp His Asp Ala Ile Gln Glu Leu Pro Pro Pro Ser
            340                 345                 350
Leu Thr Ala Gly Gly Pro Glu Asp Leu Asn Arg Val Gln Lys Ser Ala
        355                 360                 365
Leu Pro Thr Arg Thr Lys Met Ser Glu Thr Arg Ala Asp Leu Phe Ser
    370                 375                 380
Lys Leu Pro Lys Tyr Arg Thr Arg Ala Gly Glu Gly Phe Gly Tyr Ala
385                 390                 395                 400
Pro Asp Thr Leu Ala Gly Pro Val Ala Gln Gly Glu Thr Tyr Ser Phe
                405                 410                 415
Tyr Lys Ala Asn Val Ala Arg Lys Tyr Pro Gly Ser Asn Tyr Met Glu
            420                 425                 430
Arg Trp Arg Asp Asn Thr Val Asp Arg Met Leu Ser Trp Gly Phe Thr
        435                 440                 445
Ser Phe Gly Asn Trp Thr Asp Pro Glu Met Tyr Asp Asn Asp Arg Ile
    450                 455                 460
Pro Tyr Phe Ala His Gly Trp Ile Lys Gly Asp Phe Lys Thr Val Ser
```

-continued

```
                465                 470                 475                 480
        Thr Gly Gln Asp Tyr Trp Gly Pro Met Pro Asp Pro Phe Asp Pro Ala
                        485                 490                 495

Phe Ser Asp Ala Ala Ala Arg Thr Ala Arg Ala Val Ala Asp Glu Val
                        500                 505                 510

Ala Asp Ser Pro Leu Ala Ile Gly Val Phe Met Asp Asn Glu Leu Ser
                        515                 520                 525

Trp Gly Asn Ala Gly Ser Phe Ser Thr Arg Tyr Gly Val Val Ile Asp
                        530                 535                 540

Thr Met Ser Arg Asp Ala Ala Glu Ser Pro Thr Lys Ser Ala Phe Ser
        545                 550                 555                 560

Asp Glu Leu Glu Glu Lys Tyr Gly Thr Ile Asp Ala Leu Asn Ala Ala
                        565                 570                 575

Trp Gln Thr Thr Val Pro Ser Trp Glu Ala Leu Arg Ser Gly Ser Ala
                        580                 585                 590

Asp Leu Gly Ser Asp Glu Thr Ala Lys Glu Ser Asp Tyr Ser Ala Leu
                        595                 600                 605

Met Thr Leu Tyr Ala Thr Gln Tyr Phe Lys Thr Val Asp Ala Glu Leu
                        610                 615                 620

Asp Lys Val Met Pro Asp His Leu Tyr Ala Gly Ser Arg Phe Ala Ser
        625                 630                 635                 640

Trp Gly Arg Thr Pro Glu Val Val Glu Ala Ala Ser Lys Tyr Val Asp
                        645                 650                 655

Ile Met Ser Tyr Asn Glu Tyr Arg Glu Gly Leu His Pro Ser Glu Trp
                        660                 665                 670

Ala Phe Leu Glu Glu Leu Asp Lys Pro Ser Leu Ile Gly Glu Phe His
                        675                 680                 685

Met Gly Thr Thr Thr Gly Gln Pro His Pro Gly Leu Val Ser Ala
                        690                 695                 700

Gly Thr Gln Ala Glu Arg Ala Arg Met Tyr Ala Glu Tyr Met Glu Gln
        705                 710                 715                 720

Leu Ile Asp Asn Pro Tyr Met Val Gly Gly His Trp Phe Gln Tyr Ala
                        725                 730                 735

Asp Ser Pro Val Thr Gly Arg Ala Leu Asp Gly Glu Asn Tyr Asn Ile
                        740                 745                 750

Gly Phe Val Ser Val Thr Asp Arg Pro Tyr Pro Glu Ile Val Ala Ala
                        755                 760                 765

Ala Arg Asp Val Asn Gln Arg Leu Tyr Asp Arg Tyr Gly Asn Leu
                        770                 775                 780

Ala Thr Ala Glu Gly His Tyr Thr Gly Arg Arg Ser Ala Glu
        785                 790                 795

<210> SEQ ID NO 6
<211> LENGTH: 798
<212> TYPE: PRT
<213> ORGANISM: Unknown
<220> FEATURE:
<223> OTHER INFORMATION: DagB derived from Streptomyces coelicolor
      A3(2)_M22-2C43

<400> SEQUENCE: 6

Met Thr Val His Lys Arg Ala Cys Thr Thr Pro Pro Arg Ala Ser
1               5                   10                  15

Arg Ser Phe Arg Val Arg Trp Pro Val Leu Ile Ala Ala Cys Ala
                20                  25                  30
```

-continued

```
Gly Leu Val Leu Ala Thr Thr Ser Pro Pro Ala Val Ala Gly Ala
         35                  40                  45

His Asp Leu Gly Asp Glu Thr Met Leu Tyr Asp Phe Gln Asp Gly Leu
 50                  55                  60

Val Pro Ala Glu Val Gly Pro Tyr Gln Ala Lys Thr Thr Ile Val Gly
 65                  70                  75                  80

Arg Gly Asp Lys Lys Leu Arg Val Asp Phe Gln Ala Arg Lys Asn Tyr
                 85                  90                  95

Tyr Ser Ser Phe Ser Val Arg Pro Glu Pro Val Trp Asn Trp Ser Ala
                100                 105                 110

Glu Glu Ser Glu Ser Leu Gly Ile Ala Met Glu Leu Thr Asn Pro Ser
                115                 120                 125

Asp Arg Ser Val Gln Leu Thr Ile Asp Leu Glu Ser Ser Thr Gly Val
130                 135                 140

Ala Thr Arg Ser Val Asn Val Pro Ala Gly Gly Gly Thr Tyr Tyr
145                 150                 155                 160

Phe Asp Val Asp Ser Pro Ala Leu His Arg Asp Thr Gly Leu Arg Ala
                165                 170                 175

Asp Pro Ser Trp Leu Ala Asp Lys Asp Val Thr Ser Ala Val Trp Met
                180                 185                 190

Trp Gly Ser Lys Glu Thr Asp Thr Ser Arg Ile Ser Gln Leu Asn Phe
                195                 200                 205

Tyr Val Ala Gly Leu Leu His Asp Arg Ser Val Ile Val Asp Asp Ile
210                 215                 220

Arg Val Val Arg Asp Ala Pro Asp Pro Asp Tyr Leu Lys Gly Leu
225                 230                 235                 240

Val Asp Ala Phe Gly Gln Asn Asn Lys Val Asp Tyr Lys Gly Lys Val
                245                 250                 255

Ser Arg Thr Ser Glu Ile Leu Arg Gln Arg Ala Ala Glu Ala Lys Asp
                260                 265                 270

Leu Arg Arg His Pro Val Pro Glu Asp Arg Ser Arg Tyr Gly Gly Trp
                275                 280                 285

Leu Asn Gly Pro Arg Leu Glu Ala Thr Gly Asn Phe Arg Val Glu Lys
290                 295                 300

Tyr Gln Gly Arg Trp Thr Leu Val Asp Pro Asp Gly Tyr Leu Phe Phe
305                 310                 315                 320

Ser Thr Gly Ile Asp Asn Ala Arg Met Phe Asp Ser Pro Thr Thr Thr
                325                 330                 335

Gly Tyr Asp Phe Asp His Asp Ala Ile Gln Glu Leu Pro Pro Pro Ser
                340                 345                 350

Leu Thr Ala Gly Gly Pro Glu Asp Leu Asn Arg Val Gln Lys Ser Ala
                355                 360                 365

Leu Pro Thr Arg Thr Lys Met Ser Glu Thr Arg Ala Asp Leu Phe Ser
370                 375                 380

Lys Leu Pro Lys Tyr Arg Thr Arg Ala Gly Glu Gly Phe Gly Tyr Ala
385                 390                 395                 400

Pro Asp Thr Leu Ala Gly Pro Val Ala Gln Gly Glu Thr Tyr Ser Phe
                405                 410                 415

Tyr Lys Ala Asn Val Ala Arg Lys Tyr Pro Gly Ser Asn Tyr Met Glu
                420                 425                 430

Arg Trp Arg Asp Asn Thr Val Asp Arg Met Leu Ser Trp Gly Phe Thr
                435                 440                 445

Ser Phe Gly Asn Trp Thr Asp Pro Glu Met Tyr Asp Asn Asp Arg Ile
```

-continued

```
                450             455             460
Pro Tyr Phe Ala His Gly Trp Ile Lys Arg Asp Phe Lys Thr Val Ser
465                 470                 475                 480

Thr Gly Gln Asp Tyr Trp Gly Pro Met Pro Asp Pro Phe Asp Pro Ala
            485                 490                 495

Phe Ser Asp Ala Ala Ala Arg Thr Ala Arg Ala Val Ala Asp Glu Val
            500                 505                 510

Ala Asp Ser Pro Leu Ala Ile Gly Val Phe Met Asp Asn Glu Leu Ser
            515                 520                 525

Trp Gly Asn Ala Gly Ser Phe Ser Thr Arg Tyr Gly Val Val Ile Asp
            530                 535                 540

Thr Met Ser Arg Asp Ala Ala Glu Ser Pro Thr Lys Ser Ala Phe Ser
545                 550                 555                 560

Asp Glu Leu Glu Glu Lys Tyr Gly Thr Ile Asp Ala Leu Asn Ala Ala
                565                 570                 575

Trp Gln Thr Thr Val Pro Ser Trp Glu Ala Leu Arg Ser Gly Ser Ala
            580                 585                 590

Asp Leu Gly Ser Asp Glu Thr Ala Lys Glu Ser Asp Tyr Ser Ala Leu
            595                 600                 605

Met Thr Leu Tyr Ala Thr Gln Tyr Phe Lys Thr Val Asp Ala Glu Leu
            610                 615                 620

Asp Lys Val Met Pro Asp His Leu Tyr Ala Gly Ser Arg Phe Ala Ser
625                 630                 635                 640

Trp Gly Arg Thr Pro Glu Val Val Glu Ala Ala Ser Lys Tyr Val Asp
                645                 650                 655

Ile Met Ser Tyr Asn Glu Tyr Arg Glu Gly Leu His Pro Ser Glu Trp
                660                 665                 670

Ala Phe Leu Glu Glu Leu Asp Lys Pro Ser Leu Ile Gly Glu Phe His
            675                 680                 685

Met Gly Thr Thr Thr Thr Gly Gln Pro His Pro Gly Leu Val Ser Ala
            690                 695                 700

Gly Thr Gln Ala Glu Arg Ala Arg Met Tyr Ala Glu Tyr Met Glu Gln
705                 710                 715                 720

Leu Ile Asp Asn Pro Tyr Met Val Gly Gly His Trp Phe Gln Tyr Ala
                725                 730                 735

Asp Ser Pro Val Thr Gly Arg Ala Leu Asp Gly Glu Asn Tyr Asn Ile
                740                 745                 750

Gly Phe Val Ser Val Thr Asp Arg Pro Tyr Pro Glu Ile Val Ala Ala
            755                 760                 765

Ala Arg Asp Val Asn Gln Arg Leu Tyr Asp Arg Arg Tyr Gly Asn Leu
            770                 775                 780

Ala Thr Ala Glu Gly His Tyr Thr Gly Arg Arg Ser Ala Glu
785                 790                 795
```